(12) United States Patent
Duan et al.

(10) Patent No.: US 8,318,157 B2
(45) Date of Patent: Nov. 27, 2012

(54) TRICHODERMA REESEI α-AMYLASE ENHANCES SACCHARIFICATION OF CORN STARCH

(75) Inventors: Gang Duan, Shanghai (CN); Kathy Qian, Wuxi (CN); Martijn Scheffers, Leiden (NL); Jayarama K. Shetty, Pleasanton, CA (US); Pieter Van Solingen, Naaldwijk (NL)

(73) Assignee: Danisco US Inc., Palo Alto, CA (US)

( * ) Notice: Subject to any disclaimer, the term of this patent is extended or adjusted under 35 U.S.C. 154(b) by 264 days.

(21) Appl. No.: 12/532,083

(22) PCT Filed: Mar. 12, 2008

(86) PCT No.: PCT/US2008/056597
§ 371 (c)(1),
(2), (4) Date: Mar. 19, 2010

(87) PCT Pub. No.: WO2008/112727
PCT Pub. Date: Sep. 18, 2008

(65) Prior Publication Data
US 2010/0278970 A1 Nov. 4, 2010

Related U.S. Application Data

(60) Provisional application No. 60/906,812, filed on Mar. 14, 2007, provisional application No. 60/906,811, filed on Mar. 14, 2007.

(51) Int. Cl.
*A61K 38/46* (2006.01)
*C12N 9/28* (2006.01)
(52) U.S. Cl. ........................ 424/94.6; 435/202
(58) Field of Classification Search ................. 424/94.6; 435/202
See application file for complete search history.

(56) References Cited

U.S. PATENT DOCUMENTS

| | | | |
|---|---|---|---|
| RE32,153 E | 5/1986 | Tamura et al. | |
| 4,587,215 A | 5/1986 | Hirsh | |
| 5,246,853 A | 9/1993 | Clarkson et al. | |
| 5,475,101 A | 12/1995 | Ward et al. | |
| 5,650,322 A | 7/1997 | Clarkson et al. | |
| 5,874,276 A | 2/1999 | Fowler et al. | |
| 6,022,725 A | 2/2000 | Fowler et al. | |
| 6,077,316 A | 6/2000 | Lund et al. | |
| 6,268,328 B1 | 7/2001 | Mitchinson et al. | |
| 7,413,879 B2 | 8/2008 | Dunn-Coleman et al. | |
| 7,413,887 B2 | 8/2008 | Dunn-Coleman et al. | |
| 7,494,685 B2 | 2/2009 | Dunn-Coleman et al. | |
| 2010/0256345 A1 * | 10/2010 | Ochiai et al. ............... | 536/8 |

FOREIGN PATENT DOCUMENTS

| | | |
|---|---|---|
| EP | 0 135 138 A2 | 3/1985 |
| EP | 0 214 761 A2 | 3/1987 |
| EP | 0 215 594 A2 | 3/1987 |
| EP | 0 238 023 A2 | 9/1987 |
| EP | 0 244 234 A2 | 11/1987 |
| EP | 0 305 216 A1 | 3/1989 |
| WO | WO 84/02921 A2 | 8/1984 |
| WO | WO 86/01831 A1 | 3/1986 |
| WO | WO 88/02775 A1 | 4/1988 |
| WO | WO 89/01032 A1 | 2/1989 |
| WO | WO 91/18977 A1 | 12/1991 |
| WO | WO 91/19782 A1 | 12/1991 |
| WO | WO 92/00381 A1 | 1/1992 |
| WO | WO 92/01793 A1 | 2/1992 |
| WO | WO 92/06184 A1 | 4/1992 |
| WO | WO 92/06209 A1 | 4/1992 |
| WO | WO 92/17573 A1 | 10/1992 |
| WO | WO 95/00636 A1 | 1/1995 |
| WO | WO 99/28448 A1 | 6/1999 |
| WO | WO 99/43794 A1 | 9/1999 |
| WO | WO 00/04136 A1 | 1/2000 |
| WO | WO 2004/091544 A2 | 10/2004 |
| WO | WO 2005/001036 A2 | 1/2005 |
| WO | WO 2006/060062 A2 | 6/2006 |

OTHER PUBLICATIONS

Boel, E., M T Hansen, et al. "Two different types of intervening sequences in the glucoamylase gene from *Aspergillus niger*." *EMBO J.* 3(7):1581-1585, 1984.
Boel, E., I. Hjort, et al. "Glucoamylases G1 and G2 from *Aspergillus niger* are synthesized from two different but closely related mRNAs." *The EMBO Journal* 3(5):1097-1102, 1984.
Campbell, E.I. et al. "Improved transformation efficiency of *Aspergillus niger* using the homologous niaD gene for nitrate reductase." *Current Genetics* 16(1):53-56, 1989.
Cao, Q.N. et al. "Penicillopepsin-JT2, a recombinant enzyme from *Penicillium janthinellum* and the contribution of a hydrogen bond in subsite S3 to k(cat)." *Protein Sci* 9(5):991-1001, 2000.
Chen, H.M. et al. "Substitution of asparagine residues in *Aspergillus awamori* glucoamylase by site-directed mutagenesis to eliminate N-glycosylation and inactivation by deamidation." *Biochem. J.* 301(Pt 1):275-281, 1994.
Chen, H.-M. et al. "Identification and elimination by site-directed mutagenesis of thermolabile aspartyl bonds in *Aspergillus awamori* glucoamylase." *Protein Eng.* 8(6):575-582, 1995.
Chen, H.-M. et al. "Effect of replacing helical glycine residues with alanines on reversible and irreversible stability and production of *Aspergillus awamori* glucoamylase." *Protein Eng.* 9(6):499-505, 1996.
Christophersen, C. et al. "Enzymatic Characterisation of Novamyl, a Thermostable α-Amylase." *Starch—Stärke* 50(1):39-45, 1998.
Fierobe, H-P et al. "Mutational Modulation of Substrate Bond-Type Specificity and Thermostability of Glucoamylase from *Aspergillus awamori* by Replacement with Short Homologue Active Site Sequences and Thiol/Disulfide Engineering." *Biochemistry* 35(26):8696-8704, 1996.

(Continued)

*Primary Examiner* — Tekchand Saidha
(74) *Attorney, Agent, or Firm* — Danisco US Inc.

(57) ABSTRACT

A maltogenic α-amylase from *Trichoderma reesei* (TrAA) and variants thereof in the presence of a glucoamylase are useful in the production of high-glucose syrups from liquefied starch, where the high-glucose syrups produced thereby contain at least about 97% glucose. In this process, TrAA advantageously suppresses the reversion of glucose to malto-oligosaccharides. Expression hosts and encoding nucleic acids useful for producing TrAA and its variants also are provided.

7 Claims, 9 Drawing Sheets

OTHER PUBLICATIONS

Finkelstein, D.B. "Transformation." In *Biotechnology of Filamentous Fungi: Technology and Products*, eds. D.B. Finkelstein et al. Boston, MA: Butterworth-Heinemann, pp. 113-156, 1992.

Fogarty, W.M. et al. "Starch degrading enzymes of microbial origin." *Progress in Industrial Microbiology* 15:87-150, particularly 112-115, 1979.

Goedegebuur, F. et al. "Cloning and relational analysis of 15 novel fungal endoglucanases from family 12 glycosyl hydrolase." *Current Genetics* 41(2):89-98, 2002.

Goto, M. et al. "The Mechanism of Binding of Glucoamylase I from *Aspergillus awamori* var. kawachi to Cyclodextrins and Raw Starch." *Bioscience, biotechnology, and biochemistry* 58(1):49-54, 1994.

Harkki, A. et al. "Genetic engineering of *Trichoderma* to produce strains with novel cellulase profiles." *Enzyme Microb. Technol* 13(3):227-233, 1991.

Harkki, A. et al. "A Novel Fungal Expression System: Secretion of Active Calf Chymosin from the Filamentous Fungus *Trichoderma reesei*." *Bio/Technology* 7(6):596-603, 1989.

van den Hondel, C. et al. "Heterologous gene expression in filamentous fungi." In *More Gene Manipulations in Fungi*, eds. J.W. Bennett et al. San Diego, CA: Academic Press, pp. 396-428, 1991.

Ilmen, M. et al. "Regulation of cellulase gene expression in the filamentous fungus *Trichoderma reesei*." *Appl. Environ. Microbiol.* 63(4):1298-1306, 1997.

Innis, M. A. et al. "Expression, Glycosylation, and Secretion of an *Aspergillus* Glucoamylase by *Saccharomyces cerevisiae*." *Science* 228(4695):21-26, 1985.

Kelly, J.M. et al. "Transformation of *Aspergillus niger* by the amdS gene of *Aspergillus nidulans*." *The EMBO Journal* 4(2):475-479, 1985.

Li, Y. et al. "Effect of introducing proline residues on the stability of *Aspergillus awamori*." *Protein Eng.* 10(10):1199-1204, 1997.

Nevalainen, K.M.H. et al. "The Molecular Biology of *Trichoderma* and its Application to the Expression of Both Homologous and Heterologous Genes." In *Molecular Industrial Mycology*, eds. S.A. Leong et al. New York: Marcel Dekker, pp. 129-148, 1991.

Nunberg, J.H. et al. "Molecular cloning and characterization of the glucoamylase gene of *Aspergillus awamori*." *Mol. Cell. Biol.* 4(11):2306-2315, 1984.

Penttilä, M. et al. "A versatile transformation system for the cellulolytic filamentous fungus *Trichoderma reesei*." *Gene* 61(2):155-164, 1987.

Pourquié, J. et al. "Scale up of cellulase production and utilization." In *Biochemistry and Genetics of Cellulose Degradation*, eds. J.P. Aubert et al. London: Academic Press, pp. 71-86, 1988.

Sheir-Neiss, G. et al. "Characterization of the secreted cellulases of *Trichoderma reesei* wild type and mutants during controlled fermentations." *Applied Microbiology and Biotechnology* 20(1):46-53, 1984.

Ward, M. et al. "Use of *Aspergillus* overproducing mutants, cured for intergrated plasmid, to overproduce heterologous proteins." *Applied Microbiology and Biotechnology* 39(6):738-743, 1993.

* cited by examiner

FIG. 7A

SEQ ID NO:1 *Trichoderma reesei* α-amylase – genomic DNA (1548 nucleotides)

```
   1 atgaagctcc ggtacgctct cccgctgctc ttgcagctct ctttgccggt cctctccgca
  61 gacaccgccg cctggaggtc ccgcaccatc tactttgccc tgacagaccg catcgctcgt
 121 ggaagcggtg acacgggggg cagtgcgtgt gggaacctgg gggactactg cggtggcacg
 181 ttccagggct tggagagcaa gttggactac atcaagggca tgggattcga tgccatctgg
 241 atcacacctg ttgtgacgag tgagtctttt cataccttgc cctgccttgc ctcgcctcgc
 301 cttgcatgtg tcgcatacag gcttctggta tgcatagcta aacctgatac ctctggacag
 361 acagtgatgg gggctaccat ggctattggg cggaggacat cgactccatc aactctcatt
 421 atggctctgc ggacgatctc aagagtctcg tcaacgccgc gcatagcaag gtattccctt
 481 ttgttcacac cagacttcat gattatcaaa attaacacaa accagggctt ctatatgatg
 541 gtggacgtcg tggccaacca catgggctac gccaatatct ctgacgatag tccctctcca
 601 ctgaaccagg cctcgtcgta tcaccccgag tgtgatatcg actacaacaa ccaaaccagc
 661 gtcgagaact gctggatcag cggcctcccg gatctcaaca cgcagagctc aaccatccgc
 721 agcctctacc aggactgggt ctccaacctc gtgtccacgt acggcttcga cggcgtccgc
 781 atcgacaccg tcaagcacgt cgagcaagac tactggcccg gcttcgtcaa cgccaccggc
 841 gtctactgca tcggcgaggt ctttgacgga gacccaaact acctgctgcc ctacgccagc
 901 ctcatgccgg gcctgctcaa ctacgccatc tactacccca tgacgcgctt cttcctccag
 961 cagggctcct cgcaggacat ggtcaacatg cacgaccaga tcggcagcat gttccccgac
1021 ccgaccgcgc tcggcacctt tgtcgacaac cacgacaacc cgcgcttcct gagcatcaag
1081 aacgacacgg ccctgctcaa gaacgcgctg acgtacacca tcctctcgcg cggcatcccc
1141 atcgtctact acggcaccga gcaggccttc tcgggcggca acgacccggc caacaggag
1201 gacctctggc gcagcggctt caacgcccag tccgacatgt acgacgccat ctccaagctc
1261 acctacgcca agcacgccgt cgggcggcctc gccgacaacg accacaagca cctgtacgtc
1321 gccgacacgg cctacgcctt cagccgcgcc ggcggcaaca tggtggccct gaccaccaac
1381 agcggcagcg ggagctcggc ccagcactgc ttcggcacgc aggtgcccaa cggccgctgg
1441 cagaatgtct ttgacgaggg caatgggccg acgtattccg ccgacggcaa cggccagctt
1501 tgcttgaatg tgtccaacgg tcagcccatt gtcttgctgt cttcgtga
```

SEQ ID NO:2 *Trichoderma reesei* α-amylase - coding sequence (1392 nucleotides)

```
   1 atgaagctcc ggtacgctct cccgctgctc ttgcagctct ctttgccggt cctctccgca
  61 gacaccgccg cctggaggtc ccgcaccatc tactttgccc tgacagaccg catcgctcgt
 121 ggaagcggtg acacgggggg cagtgcgtgt gggaacctgg gggactactg cggtggcacg
 181 ttccagggct tggagagcaa gttggactac atcaagggca tgggattcga tgccatctgg
 241 atcacacctg ttgtgacgag tgatgatggg ggctaccatg gctattgggc ggaggacatc
 301 gactccatca actctcatta tggctctgcg gacgatctca agagtctcgt caacgccgcg
 361 catagcaagg gcttctatat gatggtggac gtcgtggcca accacatggg ctacgccaat
 421 atctctgacg atagtccctc tccactgaac caggcctcgt cgtatcaccc cgagtgtgat
 481 atcgactaca acaaccaaac cagcgtcgag aactgctgga tcagcggcct cccggatctc
 541 aacacgcaga gctcaaccat ccgcagcctc taccaggact gggtctccaa cctcgtgtcc
 601 acgtacggct tcgacggcgt ccgcatcgac accgtcaagc acgtcgagca agactactgg
 661 cccggcttcg tcaacgccac cggcgtctac tgcatcggcg aggtctttga cggagaccca
 721 aactacctgc tgccctacgc cagcctcatg ccgggcctgc tcaactacgc catctactac
 781 cccatgacgc gcttcttcct ccagcagggc tcctcgcagg acatggtcaa catgcacgac
 841 cagatcggca gcatgttccc cgaccgaccc gcgctcggca cctttgtcga caaccacgac
 901 aacccgcgct tcctgagcat caagaacgac acgggccctgc tcaagaacgc gctgacgtac
 961 accatcctct cgcgcggcat ccccatcgtc tactacggca ccgagcaggc cttctcgggc
1021 ggcaacgacc cggccaacag ggaggacctc tggcgcagcg gcttcaacgc ccagtccgac
1081 atgtacgacg ccatctccaa gctcacctac gccaagcacg ccgtcggcgg cctcgccgac
1141 aacgaccaca agcacctgta cgtcgccgac acggcctacg ccttcagccg cgccggcggc
1201 aacatggtgg ccctgaccac caacagcggc agcgggagct cggcccagca ctgcttcggc
1261 acgcaggtgc ccaacggccg ctggcagaat gtctttgacg agggcaatgg gccgacgtat
1321 tccgccgacg gcaacggcca gctttgcttg aatgtgtcca acggtcagcc cattgtcttg
1381 ctgtcttcgt ga
```

FIG. 7B

SEQ ID NO:3  *Trichoderma reesei* α-amylase - Amino acid sequence (463 amino acids)

```
  1 MKLRYALPLL LQLSLPVLSA DTAAWRSRTI YFALTDRIAR GSGDTGGSAC GNLGDYCGGT
 61 FQGLESKLDY IKGMGFDAIW ITPVVTSDDG GYHGYWAEDI DSINSHYGSA DDLKSLVNAA
121 HSKGFYMMVD VVANHMGYAN ISDDSPSPLN QASSYHPECD IDYNNQTSVE NCWISGLPDL
181 NTQSSTIRSL YQDWVSNLVS TYGFDGVRID TVKHVEQDYW PGFVNATGVY CIGEVFDGDP
241 NYLLPYASLM PGLLNYAIYY PMTRFFLQQG SSQDMVNMHD QIGSMFPDPT ALGTFVDNHD
301 NPRFLSIKND TALLKNALTY TILSRGIPIV YYGTEQAFSG GNDPANREDL WRSGFNAQSD
361 MYDAISKLTY AKHAVGGLAD NDHKHLYVAD TAYAFSRAGG NMVALTTNSG SGSSAQHCFG
421 TQVPNGRWQN VFDEGNGPTY SADGNGQLCL NVSNGQPIVL LSS
```

SEQ ID NO:4  *Trichoderma reesei* α-amylase – signal sequence (60 nucleotides)
```
  1 atgaagctcc ggtacgctct cccgctgctc ttgcagctct ctttgccggt cctctccgca
```

SEQ ID NO:5  *Trichoderma reesei* α-amylase – leader sequence (20 amino acids)
```
  1 MKLRYALPLL LQLSLPVLSA
```

SEQ ID NO:6  Forward primer NSP331 (22 nucleotides)
```
  1 atgaagctcc ggtacgctct cc
```

SEQ ID NO:7  Reverse primer NSP332 (25 nucleotides)
```
  1 tcacgaagac agcaagacaa tgggc
```

TRICHODERMA REESEI α-AMYLASE ENHANCES SACCHARIFICATION OF CORN STARCH

This application claims priority of U.S. Provisional applications 60/906,811, filed Mar. 14, 2007 and 60/906,812, filed Mar. 14, 2007, each of which is herein incorporated by reference in its entirety.

SEQUENCE LISTING

The sequence listing submitted via EFS, in compliance with C.F.R. §1.52(e), is incorporated herein by reference. The sequence listing text file submitted via EFS contains the file "30964WO sequence listing.txt", created on Oct. 13, 2011, which is 9,042 bytes in size.

A maltogenic α-amylase from *Trichoderma reesei* (TrAA), nucleic acids encoding the same, and host cells comprising the nucleic acids are provided. Methods of using TrAA include saccharification of starch to a glucose-rich syrup.

BACKGROUND

High fructose corn syrup (HFCS) is a processed form of corn syrup having a high fructose content and a sweetness comparable to sugar, making HFCS useful as a sugar substitute in soft drinks and other processed foods. HFCS currently represents a billion dollar industry. The process of producing HFCS has progressed over the years from acid hydrolysis to a sequence of enzyme-catalyzed reactions:

(1) Liquefaction: α-Amylases (EC 3.2.1.1) are first used to degrade a starch suspension containing 30-40% w/w dry solids (ds) to maltodextrans. α-Amylases are endohydrolases that catalyze the random cleavage of internal α-1,4-D-glucosidic bonds. Because liquefaction typically is conducted at high temperatures, e.g., 90-100° C., thermostable α-amylases, such as an α-amylase from *Bacillus* sp., are preferred for this step.

(2) Saccharification: Glucoamylases and/or maltogenic α-amylases commonly are used to catalyze the hydrolysis of non-reducing ends of the maltodextrans formed after liquefaction, releasing D-glucose, maltose and isomaltose. De-branching enzymes, such as pullulanase, can be used to aid saccharification. Saccharification typically takes place under acidic conditions at elevated temperatures, e.g., 60° C., pH 4.3. Glucoamylases used in this process typically are obtained from fungi, e.g., *Aspergillus niger* glucoamylase (AnGA) used in Optidex® L400 or *Humincola grisea* glucoamylase (HgGA). Maltogenic α-amylases currently used for this application include plant amylases and the α-amylase from *Aspergillus oryzae*, the active ingredient of Clarase® L. Saccharification can be used to produce either high-maltose or glucose-rich syrups.

(3) Isomerization: A glucose-rich syrup can be processed further to produce fructose, when sweeter products are desired. Isomerization of glucose to fructose is catalyzed by glucose isomerase and yields about 42% (w/v) fructose, 50-52% glucose, and a mixture of other sugars. Additional manipulations ultimately can yield commercial grade HFCS having a fructose content of 42%, 55%, or 90%, for example.

The α-amylases and glucoamylases are added directly to a process batch of corn syrup and are not reused. Glucose isomerases, on the other hand, are immobilized on columns over which the sugar mixture is passed. The glucose isomerase columns are reused until the enzymes lose most of their activity.

The saccharification step is the rate-limiting step of HFCS production. Saccharification typically occurs over 48-72 hours, by which time many fungal glucoamylases have lost significant activity. Further, although maltogenic α-amylases and glucoamylases both can be used to catalyze saccharification, the enzymes typically operate at different optimal pH and temperatures. For example, maltogenic α-amylases typically have a pH optimum of at least pH 5.0 and a temperature optimum of less than 55° C., while AnGA typically has a pH optimum of pH 4.0-4.5 and a temperature optimum of about 60° C. The difference in reaction conditions between the two enzymes necessitates adjusting the pH and temperature, which slows down the overall the process and may give rise to the formation of insoluble amylose aggregates. Any remaining bacterial α-amylase will be inactivated when the pH is lowered; however, the bacterial α-amylase may be replaced later by an acid-stable α-amylase.

Ideally, the saccharification step yields a syrup with a composition of about 95-97% w/w glucose, 1-2% w/w maltose, and 0.5-2% w/w isomaltose. This glucose-rich syrup either can be used in the isomerization reaction, step (3) above, or used for the production of crystalline glucose. These high glucose concentrations are not easily achieved. For example, *Trichoderma reesei* glucoamylase (TrGA) offers improved specific activity relative to AnGA or HgGA; however, TrGA yields a product having a final glucose concentration typically about 88% w/v. Further, high glucose concentrations in the syrup promote the conversion of glucose to maltose and maltotriose.

Accordingly, there is a need in the art for an improved process of making HFCS, which includes a saccharification step that uses an α-amylase with a pH optimum and temperature optimum compatible with the use of fungal glucoamylases. There is also a need for an α-amylase that can catalyze saccharification in less time. Further, there is a need for an α-amylase that can accomplish these objectives, while producing a syrup after saccharification that has a glucose concentration of about 96% w/w.

SUMMARY

These and other needs in the art are met by a maltogenic α-amylase from *Trichoderma reesei* (TrAA). The enzyme, variants of the enzyme, and encoding nucleic acids are provided. Host cells that express TrAA also are provided.

TrAA is advantageously used in various processes, particularly the saccharification of maltodextrans formed after liquefaction. In one embodiment, a TrAA is used in a process of maltose production either by itself or in combination with other enzymes, such as pullulanase. TrAA advantageously catalyzes maltose production at a relatively low pH and high temperature, allowing the use of reaction conditions compatible with fungal glucoamylases, e.g., AnGA. Further, the ease of producing TrAA makes it more economical than currently used α-amylases for maltose production.

In another embodiment, TrAA is used in a process of saccharification that produces a high concentration of glucose. TrAA advantageously suppresses the reverse reaction that forms maltoligosaccharides from glucose, allowing glucose concentrations in a processed corn starch mixture to reach concentrations as high as about 96% w/v. Further, this glucose concentration can be achieved in less time than if the reaction is catalyzed with only a glucoamylase. In one embodiment, a glucoamylase is added with TrAA. The glucoamylase may be a fungal glucoamylase, such as TrGA, or a blend of glucoamylases may be added, such as a combination of TrGA, HgGA, and AnGA, for example.

Accordingly, an object is to provide an isolated polypeptide comprising (i) residues 21-463 of SEQ ID NO:3, or (ii) a variant of *Trichoderma reesei* α-amylase (TrAA), wherein the variant has α-amylase activity and at least 80%, at least 90%, or at least 95% amino acid sequence identity to residues 21-463 of SEQ ID NO:3. For example, the variant may have 1-10 amino acid substitutions, insertions, or deletions compared to residues 21-463 of SEQ ID NO:3. Alternatively, the polypeptide may comprise SEQ ID NO:3 or residues 21-463 of SEQ ID NO:3, i.e., the mature polypeptide sequence absent the signal sequence. The polypeptide may comprise a signal sequence from a species other than *Trichoderma reesei*. The polypeptide in one embodiment is glycosylated. The isolated polypeptide further may be purified.

Another object is to provide a polynucleotide that encodes a polypeptide above. The polynucleotide may comprise SEQ ID NO:2, i.e., a cDNA sequence. An isolated mRNA is also provided, where the T residues in SEQ ID NO:2 are substituted with U (uracil) residues.

Another object is to provide a vector comprising the polynucleotide above, and a bacterial cell comprising this vector. A host cell that expresses the polynucleotide is also provided, where the host cell in one embodiment is a *Trichoderma* sp., particularly *T. reesei*. The host alternatively may be an RL-P37 isolate, a filamentous fungal cell, an *Aspergillus* sp., a *Fusarium* sp., or a *Penicillium* sp. The *Aspergillus* host cell may be *Aspergillus nidulans, A. awamori, A. oryzae, A. aculeatus, A. niger,* or *A. japonicus*. The *Fusarium* host cell may be *Fusarium oxysporum*, or *F. solani*. The host cell further may express a nucleic acid encoding a heterologous glucoamylase, i.e., a glucoamylase that is not the same species as the host cell. The glucoamylase, for example, may be a *Humicola grisea* glucoamylase. The host cell alternatively or in addition may not express a host cell endogenous glucoamylase.

Another object is to provide a method of saccharifying starch comprising: adding to a liquefied starch solution a polypeptide set forth above, and saccharifying the liquefied starch solution. The polypeptide may be added to the liquefied starch solution at about 0.3-1 kg per metric ton of dry solids. The liquefied starch solution may be a slurry of liquefied starch at about 20-35% w/w dry solids.

The method further may comprise a step of adding a glucoamylase to the liquefied starch solution, where saccharifying the liquefied starch solution produces a glucose-rich syrup. The glucose concentration in the glucose-rich syrup may reach at least about 97% w/w ds. The maximum concentration of glucose in the glucose-rich syrup may be reached within about 24 hours from the adding of the polypeptide to the liquefied starch solution. The glucoamylase may be derived from plants, fungi, or bacteria. For example, the glucoamylase may be *Trichoderma reesei* glucoamylase (TrGA), *Aspergillus niger* glucoamylase (AnGA), or a *Humicola grisea* glucoamylase (HgGA). The glucoamylase may be derived from a fungus that is *Aspergillus* sp., *A. awamori, A. oryzae, Talaromyces* sp, *T. emersonii, T. leycettanus, T. duponti, T. thermophilus, Clostridium* sp., *C. thermoamylolyticum,* or *C. thermohydrosulfuricum*. The glucoamylase may be added in an amount of about 0.02-2.0 GAU/g ds, or about 0.1-1.0 GAU/g ds. Other enzymes may additionally be added, including, but not limited to, a debranching enzyme, an isoamylase, a pullulanase, a protease, a cellulase, a hemicellulase, a lipase, a cutinase, or a combination thereof. The method of saccharifying starch further may comprise fermenting the saccharified starch solution to produce ethanol. The liquefied starch solution may be at about 40° C. to about 60° C. The liquefied starch solution may at about pH 4.0 to about pH 6.0, or about pH 4.2 to about pH 4.8.

It is a further object to provide a starch processing composition comprising the polypeptide above and optionally a glucoamylase, a pullulanase, a β-amylase, a fungal α-amylase that is not TrAA, a protease, a cellulase, a hemicellulase, a lipase, a cutinase, an isoamylase, or a combination thereof.

It is another object to provide a baking composition comprising the polypeptide above in a solution or in a gel. A method of baking comprises adding the baking composition of claim 1 to a substance to be baked, and baking the substance.

It is yet a further object to provide a textile desizing composition comprising the polypeptide in an aqueous solution, and optionally with another enzyme. A method of desizing a textile comprises contacting the desizing composition with a textile for a time sufficient to desize the textile.

BRIEF DESCRIPTION OF THE DRAWINGS

The accompanying drawings are incorporated in and constitute a part of this specification and illustrate various embodiments. In the drawings:

FIG. 7A and FIG. 7B are a listing of SEQ ID NOS:1-7.

DETAILED DESCRIPTION

Figure 1:
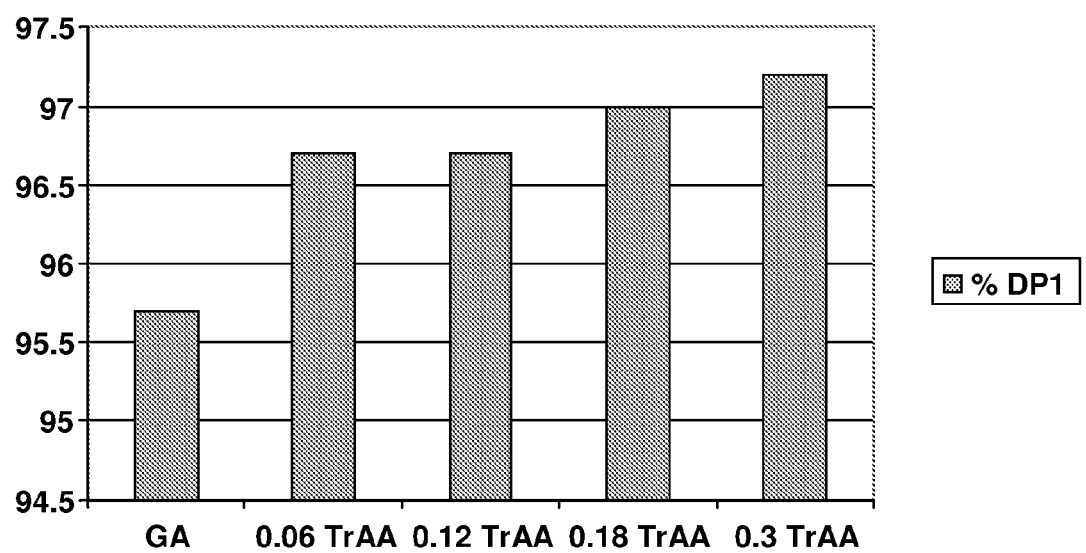
FIG. 1 depicts the ability of TrAA in the presence of glucoamylase with to catalyze a saccharification process an efficiency superior to that achieved by glucoamylase alone. The y-axis shows the weight percent of glucose (DP1) produced after 24 hours of a saccharification process at pH 4.2, 60° C. The reaction was catalyzed by either 1.0 kg/mt ds glucoamylase alone (GA) or GA combined with the indicated amount of TrAA in kg/mt ds. Note that the addition of 1 mg enzyme to a 50 mL solution containing 32% dry solids, for example, means that the solution contains 1 mg enzyme/16 g ds, or 0.0625 kg/mt ds.

A fungal α-amylase is provided from *Trichoderma reesei*. TrAA offers several advantages over currently used α-amylases. First, TrAA is active at a relatively low pH and high temperature, allowing the enzyme to be used in combination with a fungal glucoamylase under the same reaction conditions. This obviates the necessity of running a saccharification reaction as a batch process, where the pH and temperature must be readjusted for optimal use of the α-amylase or glucoamylase. Second, in combination with a pullulanase, TrAA catalyzes maltose generation with the same efficiency as commonly used, more expensive enzymes, such as Clarase® L.

1. Definitions & Abbreviations

In accordance with this detailed description, the following abbreviations and definitions apply. It should be noted that as used herein, the singular forms "a," "an," and "the" include plural referents unless the context clearly dictates otherwise. Thus, for example, reference to "an enzyme" includes a plurality of such enzymes, and reference to "the formulation" includes reference to one or more formulations and equivalents thereof known to those skilled in the art, and so forth.

Unless defined otherwise, all technical and scientific terms used herein have the same meaning as commonly understood by one of ordinary skill in the art. The following terms are provided below.

1.1. Definitions

"Amylase" means an enzyme that is, among other things, capable of catalyzing the degradation of starch. Generally, α-amylases (EC 3.2.1.1; α-D-(1→4)-glucan glucanohydrolase) are defined as endo-acting enzymes cleaving α-D-(1→4) O-glycosidic linkages within the starch molecule in a random fashion. In contrast, the exo-acting amylolytic enzymes, such as maltogenic α-amylases (EC 3.2.1.133); β-amylases (EC 3.2.1.2; and α-D-(1→4)-glucan maltohydrolase) cleave the starch molecule from the non-reducing end of the substrate. β-Amylases, α-glucosidases (EC 3.2.1.20; α-D-glucoside glucohydrolase), glucoamylase (EC 3.2.1.3; α-D-(1→4)-glucan glucohydrolase), and product-specific amylases can produce malto-oligosaccharides of a specific length from starch. Glucoamylases release glucosyl residues from the non-reducing ends of amylose and amylopectin molecules. Glucoamylases also catalyze the hydrolysis of α-1,6 and α-1,3 linkages, although at much slower rate than α-1,4 linkages.

"α-Amylase variant," "α-amylase variant polypeptide," and "variant enzyme" mean an α-amylase protein that has an amino acid sequence that has been modified from the amino acid sequence of a wild-type α-amylase. As used herein, "parent enzymes," "parent sequence," "parent polypeptide," "wild-type α-amylase protein," and "parent polypeptides" mean enzymes and polypeptides from which the α-amylase variant polypeptides are based, e.g., a *Trichoderma reesei* α-amylase. By "parent nucleic acid" is meant a nucleic acid sequence encoding the parent polypeptide. A wild-type α-amylase occurs naturally. "α-Amylase variants" differ from a wild-type α-amylase in the amino acid residues of the mature protein, i.e., without a signal sequence. The α-amylase variant can be a fusion protein containing a heterologous α-amylase polypeptide. For example, the α-amylase protein can comprise a mature α-amylase protein linked to the signal peptide of another α-amylase.

"Variants" refer to polypeptides and nucleic acids. The term "variant" may be used interchangeably with the term "mutant." Variants include insertions, substitutions, transversions, truncations, and/or inversions at one or more locations in the amino acid or nucleotide sequence, respectively. Variant nucleic acids can include sequences that are complementary to sequences that are capable of hybridizing to the nucleotide sequences presented herein. For example, a variant sequence is complementary to sequences capable of hybridizing under stringent conditions, e.g., 50° C. and 0.2×SSC (1×SSC=0.15 M NaCl, 0.015 M sodium citrate, pH 7.0), to the nucleotide sequences presented herein. More particularly, the term variant encompasses sequences that are complementary to sequences that are capable of hybridizing under highly stringent conditions, e.g., 65° C. and 0.1×SSC, to the nucleotide sequences presented herein.

As used herein, the term "expression" refers to the process by which a polypeptide is produced based on the nucleic acid sequence of a gene. The process includes both transcription and translation.

"Isolated" means that the sequence is at least substantially free from at least one other component that the sequence is naturally associated and found in nature.

"Purified" means that the material is in a relatively pure state, e.g., at least about 90% pure, at least about 95% pure, or at least about 98% pure.

"Thermostable" means the enzyme retains activity after exposure to elevated temperatures. The thermostability of an enzyme, such as an α-amylase, is measured by its half-life ($t_{1/2}$), where half of the enzyme activity is lost by the half-life. The half-life value is calculated under defined conditions by measuring the residual amylase activity.

"pH range" means the ability of the enzyme to exhibit catalytic activity from acidic to basic conditions spanning 5 or more pH units.

As used herein, "pH stable" relates to the ability of the enzyme to retain activity over a wide range of pHs.

As used herein, "amino acid sequence" is synonymous with the term "polypeptide" and/or the term "protein." In some instances, the term "amino acid sequence" is synonymous with the term "peptide"; in some instances, the term "amino acid sequence" is synonymous with the term "enzyme."

As used herein, "nucleotide sequence" or "nucleic acid sequence" refers to an oligonucleotide sequence or polynucleotide sequence and variants, homologues, fragments and derivatives thereof. The nucleotide sequence may be of genomic, synthetic or recombinant origin and may be double-stranded or single-stranded, whether representing the sense or anti-sense strand. As used herein, the term "nucleotide sequence" includes genomic DNA, cDNA, synthetic DNA, and RNA.

"Homologue" means an entity having a certain degree of identity or "homology" with the subject amino acid sequences and the subject nucleotide sequences. A "homologous sequence" includes a polynucleotide or a polypeptide having a certain percent, e.g., 80%, 85%, 90%, 95%, or 99%, of sequence identity with another sequence. Percent identity means that, when aligned, that percentage of bases or amino acid residues are the same when comparing the two sequences. Amino acid sequences are not identical, where an amino acid is substituted, deleted, or added compared to the subject sequence. The percent sequence identity typically is measured with respect to the mature sequence of the subject protein, i.e., following posttranslational modification to remove a signal sequence, for example. Typically, homologues will comprise the same active site residues as the subject amino acid sequence. Homologues also retain maltogenic α-amylase activity, although the homologue may have different enzymatic properties than the subject protein.

As used herein, "hybridization" includes the process by which a strand of nucleic acid joins with a complementary strand through base pairing, as well as the process of amplification as carried out in polymerase chain reaction (PCR) technologies. The α-amylase variant nucleic acid may exist as single- or double-stranded DNA or RNA, an RNA/DNA heteroduplex or an RNA/DNA copolymer. As used herein, "copolymer" refers to a single nucleic acid strand that comprises both ribonucleotides and deoxyribonucleotides. The α-amylase variant nucleic acid may be codon-optimized to further increase expression.

As used herein, a "synthetic" compound is produced by in vitro chemical or enzymatic synthesis. It includes, but is not limited to, α-amylase variant nucleic acids made with optimal codon usage for host organisms, such as the methylotrophic yeasts *Pichia, Hansenula, Streptomyces*, and *Trichoderma*, e.g., *T. reesei*, or other expression hosts of choice.

As used herein, "transformed cell" includes cells, including both bacterial and fungal cells, that have been transformed by use of recombinant DNA techniques. Transformation typically occurs by insertion of one or more nucleotide sequences into a cell. The inserted nucleotide sequence may be a heterologous nucleotide sequence, i.e., is a sequence that is not natural to the cell that is to be transformed, such as a fusion protein.

As used herein, "operably linked" means that the described components are in a relationship permitting them to function in their intended manner. For example, a regulatory sequence operably linked to a coding sequence is ligated in such a way that expression of the coding sequence is achieved under condition compatible with the control sequences.

As used herein, "biologically active" refers to a sequence having a similar structural, regulatory or biochemical function as the naturally occurring sequence, although not necessarily to the same degree.

The term "filamentous fungi" refers to all filamentous forms of the subdivision Eumycotina. See Alexopoulos, INTRODUCTORY MYCOLOGY, Wiley, New York (1962). These fungi are characterized by a vegetative mycelium with a cell wall composed of chitin, cellulose, and other complex polysaccharides. Filamentous fungi are morphologically, physiologically, and genetically distinct from yeasts. Vegetative growth by filamentous fungi is by hyphal elongation, and carbon catabolism is obligatory aerobic. A filamentous fungal parent cell may be a cell of *Trichoderma* sp., e.g., *T. reesei* (previously classified as *T. longibrachiatum* and currently also known as *Hypocrea jecorina*), *T. viride, T. koningii, T. harzianum*; *Penicillium* sp.; *Humicola* sp., e.g., *H. insolens* and *H. grisea*; *Chrysosporium* sp., e.g., *C. lucknowense*; *Gliocladium* sp.; *Aspergillus* sp., e.g., *A. oryzae, A. niger*, and *A. awamori*; *Fusarium* sp.; *Neurospora* sp.; *Hypocrea* sp.; and *Emericella* sp. See also Innis et al., *Science* 228: 21-26 (1985).

As used herein the term "starch" refers to any material comprised of the complex polysaccharide carbohydrates of plants, comprised of amylose and amylopectin with the formula $(C_6H_{10}O_5)_x$, where X can be any number. The term "granular starch" refers to raw, i.e., uncooked starch, e.g., starch that has not been subject to gelatinization.

As used herein the term "saccharification" refers to enzymatic conversion of starch to glucose.

The term "liquefaction" refers to the stage in starch conversion in which gelatinized starch is hydrolyzed to give low molecular weight soluble dextrins. The term "degree of polymerization" (DP) refers to the number (n) of anhydroglucopyranose units in a given saccharide. Examples of DP1 are the monosaccharides glucose and fructose. Examples of DP2 are the disaccharides maltose and sucrose.

As used herein the term "dry solids content" (ds) refers to the total solids of a slurry in a dry weight percent basis. The term "slurry" refers to an aqueous mixture containing insoluble solids.

The term "DE," or "dextrose equivalent," is defined as the percentage of reducing sugar, i.e., D-glucose, as a fraction of total carbohydrate in a syrup.

The phrase "simultaneous saccharification and fermentation (SSF)" refers to a process in the production of biochemicals in which a microbial organism, such as an ethanol producing microorganism and at least one enzyme, such as TrAA or a variant thereof, are present during the same process step. SSF refers to the contemporaneous hydrolysis of granular starch substrates to saccharides, including glucose, and the fermentation of the saccharides into alcohol, for example, in the same reactor vessel.

As used herein "ethanologenic microorganism" refers to a microorganism with the ability to convert a sugar or oligosaccharide to ethanol.

1.2. Abbreviations

The following abbreviations apply unless indicated otherwise:

| | |
|---|---|
| ADA | azodicarbonamide |
| AnGA | *Aspergillus niger* glucoamylase |
| ATCC | American Type Culture Collection |
| BBA | Spezyme ® BBA 1500 L β-amylase |
| cDNA | complementary DNA |
| DE | Dextrose Equivalent |
| DEAE | diethylamino ethanol |
| DNA | deoxyribonucleic acid |
| DNS | 3,5-dinitrosalicylic acid |
| DPn | degree of polymerization with n subunits |
| ds | dry solid |
| EC | enzyme commission for enzyme classification |
| EDTA | ethylenediaminetetraacetic acid |
| FGSC | Fungal Genetics Stock Center |
| G173A | glycine (G) residue at position 173 is replaced with an alanine (A) residue, where amino acids are designated by single letter abbreviations commonly known in the art |
| GA | glucoamylase |
| GAU | glucoamylase activity unit |
| HFCS | high fructose corn syrup |
| HFSS | high fructose starch based syrup |
| HPLC | High Performance Liquid Chromatography |
| HgGA | *Humincola grisea* glucoamylase |
| HS | higher sugars (DPn, where n > 3) |
| kb | kilobase |
| LAT | *B. licheniformis* α-amylase |
| LB | Luria Bertani broth |
| LU | Lipase Units, a measure of phospholipase activity per unit mass of enzyme |
| MOPS | 3-(n-morpholino) propanesulfonic acid |
| mRNA | messenger ribonucleic acid |
| mt | metric ton (1000 kg) |
| PCR | polymerase chain reaction |
| PEG | polyethyleneglycol |
| ppm | parts per million |
| PU | pullulanase or pullulanase units |
| RT-PCR | reverse transcriptase polymerase chain reaction |
| SD | Sabouraud Dextrose broth |
| SDS-PAGE | sodium dodecyl sulfate-polyacrylamide gel electrophoresis |
| SKBU/g ds | α-Amylase Unit per gram of dry solids. One α-Amylase Unit dextrinizes 1.0 g of limit-dextrin substrate per hour under the conditions of the assay. |
| 1X SSC | 0.15 M NaCl, 0.015 M sodium citrate, pH 7.0 |
| SSF | simultaneous saccharification and fermentation |
| TE | 10 mM Tris, pH 7.4, 1 mM EDTA |
| TrAA | *Trichoderma reesei* α-amylase |
| TrGA | *Trichoderma reesei* glucoamylase |
| w/v | weight/volume |

| | -continued |
|---|---|
| w/w | weight/weight |
| YM | Yeast Malt Extract broth |
| μL | microliter |

2. *Trichoderma reesei* α-Amylase (TrAA) and Variants Thereof

An isolated and/or purified polypeptide comprising SEQ ID NO:3 is provided. This is a wild-type *Trichoderma reesei* α-amylase (TrAA) comprising a 20 amino acid leader sequence. In one embodiment, the TrAA is a mature form of the polypeptide, wherein the 20 amino acid leader sequence is cleaved, so that the N-terminus of the polypeptide begins at the aspartic acid (D) residue at position 21 of SEQ ID NO:3. Nucleic acids encoding the polypeptide comprising SEQ ID NO:3 or amino acid residues 21-463 of SEQ ID NO:3 also are provided. In one embodiment, a nucleic acid encoding TrAA is a genomic DNA comprising SEQ ID NO:1; in another embodiment, the nucleic acid is a cDNA comprising SEQ ID NO:2. As is well understood by one skilled in the art, the genetic code is degenerate, meaning that multiple codons in some cases may encode the same amino acid. Nucleic acids include genomic DNA, mRNA and cDNA that encodes a TrAA or variant thereof.

In addition to the wild-type *Trichoderma reesei* α-amylase (TrAA), variants thereof are provided that differ from the wild-type TrAA sequence shown in SEQ ID NO:3 by the substitution, insertion, or deletion of one or more amino acids. For example, a variant α-amylase may comprise 1, 2, 3, 4, 5, 6, 7, 8, 9, 10, 11, 12, 13, 14, 15, 20, 25, 30, 35, or 40 amino acid modifications, e.g., 1-10 amino acid substitutions, while retaining maltogenic α-amylase activity. The variant TrAA may retain a higher or lower specific activity than the wild-type TrAA. The variants are synonymous with "homologues." Variant nucleic acids are provided that encode the variant polypeptides. Variant nucleic acids include all nucleic acids that encode the variant polypeptides.

2.1. TrAA Variant Characterization

Enzyme variants can be characterized by their nucleic acid and primary polypeptide sequences, by three dimensional structural modeling, and/or by their specific activity. Additional characteristics of the TrAA variant include stability, pH range, oxidation stability, and thermostability, for example. In one aspect, the TrAA variants are expressed at higher levels than the wild-type TrAA, while retaining the performance characteristics of the wild-type TrAA. Levels of expression and enzyme activity can be assessed using standard assays known to the artisan skilled in this field. In another aspect, variants demonstrate improved performance characteristics relative to the wild-type enzyme, such as improved stability at high temperatures (i.e., 70-120° C.) and/or pH extremes (i.e., pH 4.0 to 6.0, or pH 8.0 to 11.0).

An expression characteristic means an altered level of expression of the variant, when the variant is produced in a particular host cell. Expression generally relates to the amount of active variant that is recoverable from a fermentation broth using standard techniques known in this art over a given amount of time. Expression also can relate to the amount or rate of variant produced within the host cell or secreted by the host cell. Expression also can relate to the rate of translation of the mRNA encoding the variant enzyme.

TrAA variants also may have altered oxidation stability in comparison to the parent α-amylase. For example, decreased oxidation stability may be advantageous in composition for starch liquefaction.

The variant TrAA may be more thermostable than the wild-type α-amylase. Such TrAA variants are advantageous for use in baking or other processes that require elevated temperatures. For example, a thermostable TrAA variant can degrade starch at temperatures of about 55° C. to about 80° C. or more. A thermostable TrAA variant may retain its activity after exposure to temperatures of up to about 95° C.

The α-amylase variant polypeptides described herein can also have mutations that extend half-life relative to the parent enzyme by 10%, 20%, 30%, 40%, 50%, 60%, 70%, 80%, 90%, 100%, 200% or more, particularly at elevated temperatures of about 55° C. to about 95° C. or more, particularly at about 80° C. In one embodiment, the TrAA variant can be heated for about 1-10 minutes at 80° C. or higher.

The TrAA variant polypeptides further can include mutations in the signal sequence of the parent polypeptide, or elsewhere in the TrAA parent polypeptide. For example, the TrAA variant can be in the form of a fusion protein comprising a heterologous polypeptide, such as the signal peptide from *B. licheniformis* (LAT), fused to TrAA to promote secretion of the expressed protein from a bacterial host cell. Other heterologous polypeptides that may be fused to the variant TrAA include sequences to facilitate purification of the expressed protein, for example. In one embodiment, a heterologous sequence includes a protease sensitive site that allows the heterologous sequence to be cleaved from the expressed variant TrAA.

In one aspect, the TrAA variant polypeptide encoded by the nucleic acid has the same pH stability as the parental sequence. In another aspect, the TrAA variant comprises a mutation that confers a greater pH stability range or shifts the pH range to a desired area for the end commercial purpose of the enzyme. For example, in one embodiment, the TrAA variant can degrade starch at about pH 4.5 to about pH 10.5. The TrAA variant polypeptide may have a longer half-life or higher activity (depending on the assay) compared to the parent polypeptide under identical conditions, or the TrAA variant may have the same activity as the parent polypeptide. The α-amylase variant polypeptide also may have about 10%, 20%, 30%, 40%, 50%, 60%, 70%, 80%, 90%, 100%, 200% or longer half-life compared to their parent polypeptide under identical pH conditions. Alternatively, or in addition, the TrAA variant may have higher specific activity compared to the parent polypeptide under identical pH conditions.

In another aspect, a nucleic acid complementary to a nucleic acid encoding any of the TrAA variants set forth herein is provided. Additionally, a nucleic acid capable of hybridizing to the complement is provided. In another embodiment, the sequence for use in the methods and compositions described here is a synthetic sequence. It includes, but is not limited to, sequences made with optimal codon usage for expression in host organisms, such as the methylotrophic yeasts *Trichoderma*, *Pichia*, and *Hansenula*.

3. Production of TrAA and Variants Thereof

In one embodiment, wild-type TrAA is expressed in a *T. reesei* strain and optionally is isolated prior to use. In another embodiment, the wild-type TrAA is purified, following expression. Particularly useful *T. reesei* strains are selected using techniques well known to the skilled artisan that express the wild-type TrAA at high levels. High-level expression can be about 12-20 g of TrAA or a variant thereof per liter of culture medium, about 14-18 g/L, or about 16-19 g/L. In other embodiments, the wild-type TrAA or a variant thereof is recombinantly expressed in a host cell. The TrAA gene can be cloned and expressed as described, for example, in U.S. Published Applications No. 2007/0004018 and No. 2006/0094080.

Recombinantly Expressed Enzymes

In some embodiments, microorganisms are genetically engineered to express TrAA or its variants. Suitable host cells include filamentous fungal cells, which may be a strain of *Aspergillus* sp., *Trichoderma* sp., *Fusarium* sp. or *Penicillium* sp., for example. Particularly suitable fungal host cells include *Aspergillus nidulans, A. awamori, A. oryzae, A. aculeatus, A. niger, A. japonicus, Trichoderma reesei, T. viride, Fusarium oxysporum*, and *F. solani*. *Aspergillus* strains are disclosed in Ward et al., *Appl. Microbiol. Biotechnol.* 39: 738-743 (1993) and Goedegebuur et al., *Curr. Gene.* 41: 89-98 (2002). In a particularly suitable embodiment, the host is a strain of *Trichoderma reesei* that produces TrAA at relatively high levels, e.g., 15-20 g/L. Suitable *T. reesei* are known, and nonlimiting examples include ATCC No. 13631, ATCC No. 26921, ATCC No. 56764, ATCC No. 56765, ATCC No. 56767 and NRRL 15709. In some embodiments, the host strain is a derivative of RL-P37, which is disclosed in Sheir-Neiss et al., *Appl. Microbiol. Biotechnology* 20: 46-53 (1984). When TrAA or its variants are expressed in a eukaryotic host cell, the expressed TrAA in a particularly suitable embodiment has the same pattern of glycosylation as found in the wild-type TrAA. Particularly suitable host cells include *Trichoderma reesei* host cells engineered according to the procedures set forth in U.S. Pat. No. 5,874,276 and WO 05/001036 (Genencor International, Inc.).

In other embodiments, the host cell will be a genetically engineered host cell with inactivated native genes, e.g., deleted genes. For example, inactivating one or more genes in a fungal host cell may employ known methods, such as those described in U.S. Pat. Nos. 5,246,853, 5,475,101 and WO92/06209. Gene inactivation may be accomplished by complete or partial deletion, by insertional inactivation, or by any other means which renders a gene nonfunctional for its intended purpose, such that the gene is prevented from expression of a functional protein. Inactivated genes can include, for example, genes encoding cellulolytic enzymes, such as endoglucanases and exocellobiohydrolases, e.g., cbh1, cbh2, egl1, egl2 and egl3. In one embodiment, when the host cell is a *Trichoderma* cell, particularly a *T. reesei* host cell, the cbh1, cbh2, egl1 and egl2 genes will be inactivated and particularly deleted. Particularly suitable *T. reesei* host cells having quad-deleted proteins are set forth and described in U.S. Pat. No. 5,874,276 and WO 05/001036. In another embodiment, U.S. Pat. No. 5,650,322 discloses derivative strains of RL-P37 having deletions in the cbh1 gene and the cbh2 gene, for example.

In another embodiment, suitable host cells include a Gram positive bacterium selected from the group consisting of *Bacillus subtilis, B. licheniformis, B. lentus, B. brevis, B. stearothermophilus, B. alkalophilus, B. amyloliquefaciens, B. coagulans, B. circulans, B. lautus, B. thuringiensis, Streptomyces lividans*, or *S. murinus*; or a Gram negative bacterium, wherein said Gram negative bacterium is *Escherichia coli* or a *Pseudomonas* species.

In some embodiments, a host cell is genetically engineered to express an TrAA variant with an amino acid sequence having at least 80%, 85%, 90%, 95%, 96%, 97%, 98% or 99% identity with the wild-type TrAA. In some embodiments, the polynucleotide encoding a TrAA or variant thereof will have a nucleic acid sequence of SEQ ID NO:2 or a nucleic acid sequence having at least 80%, 85%, 90%, 95%, 96%, 97%, 98% or 99% sequence identity with SEQ ID NO:2. In other embodiments, the host strain expressing a TrAA or variant thereof also is genetically engineered to express a heterologous GA.

3.2. Vectors

In some embodiments, a DNA construct comprising a nucleic acid encoding a TrAA or variant thereof is constructed to be expressed in a host cell. Representative nucleic acids that encode TrAA include SEQ ID NO:1 and 2. In one embodiment, the DNA construct is transferred to a host cell by an expression vector that comprises regulatory sequences operably linked to a TrAA coding sequence.

The vector may be any vector that can be integrated into a fungal host cell genome and replicated when introduced into the host cell. The FGSC Catalogue of Strains (lists suitable vectors. See FGSC, Catalogue of Strains, University of Missouri, at www.fgsc.net (last modified Jan. 17, 2007). Additional examples of suitable expression and/or integration vectors are provided in Sambrook et al., MOLECULAR CLONING: A LABORATORY MANUAL, 3$^{rd}$ ed., Cold Spring Harbor Laboratory Press, Cold Spring Harbor, N.Y. (2001); Bennett et al., MORE GENE MANIPULATIONS IN FUNGI, Academic Press, San Diego (1991), pp. 396-428; and U.S. Pat. No. 5,874,276. Particularly useful vectors include pFB6, pBR322, PUC18, pUC100 and pENTR/D, pDON™ 201, pDONR™ 221, pENTR™, pGEM® 3Z and pGEM® 4Z. Suitable plasmids for use in bacterial cells include pBR322 and pUC19, which permit replication in *E. coli*, and pE194, for example, which permits replication in *Bacillus*.

In some embodiments, a nucleic acid encoding a TrAA or a variant thereof is operably linked to a suitable promoter, which allows transcription in the host cell. The promoter may be derived from genes encoding proteins either homologous or heterologous to the host cell. Preferably, the promoter is useful in a *Trichoderma* host. Suitable nonlimiting examples of promoters include cbh1, cbh2, egl1, and egl2 promoters. In one embodiment, the promoter is one that is native to the host cell. For example, when *T. reesei* is the host, the promoter is a native *T. reesei* promoter. In one embodiment, the promoter is *T. reesei* cbh1, which is an inducible promoter that is deposited in GenBank under Accession No. D86235. An "inducible promoter" is a promoter that is active under environmental or developmental regulation. In another embodiment, the promoter is one that is heterologous to the host cell. Other examples of useful promoters include promoters from *Aspergillus awamori* and *A. niger* glucoamylase genes. See Nunberg et al., *Mol. Cell. Biol.* 4: 2306-2315 (1984) and Boel et al., *EMBO J.* 3: 1581-1585 (1984).

In some embodiments, the coding sequence is operably linked to a signal sequence. The DNA encoding the signal sequence may be the DNA sequence naturally associated with the TrAA gene to be expressed. For example, the encoding DNA may comprise the nucleotide sequence of SEQ ID NO:4, which encodes the TrAA signal sequence of SEQ ID NO:5. In other embodiments, the encoding DNA does not comprise SEQ ID NO:4, which is replaced with a nucleotide sequence encoding a signal sequence from a species other than *Trichoderma reesei*. In this embodiment, the polynucleotide that encodes the signal sequence is immediately upstream and in frame of the polynucleotide that encodes the polypeptide. In additional embodiments, a signal sequence and a promoter sequence comprising a DNA construct or vector to be introduced into a fungal host cell are derived from the same source. For example, in some embodiments, the signal sequence is the cbh1 signal sequence that is operably linked to a cbh1 promoter.

In some embodiments, the expression vector also includes a termination sequence. In one embodiment, the termination sequence and the promoter sequence are derived from the same source. In another embodiment, the termination sequence is homologous to the host cell. A particularly suitable terminator sequence is cbh1 derived from a *Trichoderma* strain and particularly *T. reesei*. Other useful fungal terminators include the terminator from *Aspergillus niger* or *A. awamori* glucoamylase gene. See Nunberg et al. (1984), supra, and Boel et al. (1984), supra.

In some embodiments, an expression vector includes a selectable marker. Examples of suitable selectable markers include those that confer resistance to antimicrobial agents, e.g., hygromycin or phleomycin. Nutritional selective markers also are suitable and include amdS, argB, and pyr4. Markers useful in vector systems for transformation of *Trichoderma* are known in the art. See, e.g., BIOTECHNOLOGY OF FILAMENTOUS FUNGI, Finkelstein et al., eds., Butterworth-Heinemann, Boston, Mass. (1992), Chap. 6; and Kinghorn et al., APPLIED MOLECULAR GENETICS OF FILAMENTOUS FUNGI, Blackie Academic and Professional, Chapman and Hall, London (1992). In one embodiment, the selective marker is the amdS gene, which encodes the enzyme acetamidase; it allows transformed cells to grow on acetamide as a nitrogen source. The use of an *A. nidulans* amdS gene as a selective marker is described in Kelley et al., *EMBO J.* 4: 475-479 (1985) and Penttila et al., *Gene* 61: 155-164 (1987).

A suitable expression vector comprising a DNA construct with a polynucleotide encoding a TrAA or variant thereof may be any vector that is capable of replicating autonomously in a given host organism or integrating into the DNA of the host. In some embodiments, the expression vector is a plasmid. In some embodiments, two types of expression vectors for obtaining expression of genes are contemplated. The first expression vector comprises DNA sequences in which the promoter, TrAA coding region, and terminator all originate from the gene to be expressed. In some embodiments, gene truncation is obtained by deleting undesired DNA sequences, e.g., DNA encoding unwanted domains, to leave the domain to be expressed under control of its own transcriptional and translational regulatory sequences. The second type of expression vector is preassembled and contains sequences required for high-level transcription and a selectable marker. In some embodiments, the coding region for a TrAA gene or part thereof is inserted into this general-purpose expression vector, such that it is under the transcriptional control of the expression construct promoter and terminator sequences. In some embodiments, genes or part thereof are inserted downstream of the strong cbh1 promoter.

Methods used to ligate a DNA construct comprising a polynucleotide encoding a TrAA or variant thereof, a promoter, a terminator and other sequences and methods to insert the construct into a suitable vector are well known in the art. Linking is generally accomplished by ligation at convenient restriction sites. If such sites do not exist, the synthetic oligonucleotide linkers are used in accordance with conventional practice. See, e.g., Sambrook (2001), supra, and Bennett et al. (1991), supra. Additionally, vectors can be constructed using known recombination techniques well known in the art.

Known methods may be used to obtain a fungal host cell having one or more inactivated genes, as disclosed, for example, in U.S. Pat. Nos. 5,246,853; 5,475,101; and WO 92/06209. Gene inactivation may be accomplished by complete or partial deletion, by insertional inactivation or by any other means that renders a gene nonfunctional for its intended purpose, such that the gene is prevented from expression of a functional protein. Any gene from a *Trichoderma* sp. or other filamentous fungal host that has been cloned can be deleted, for example, cbh1, cbh2, egl1, and egl2 genes. In some embodiments, gene deletion may be accomplished by inserting a form of the desired gene to be inactivated into a plasmid by methods known in the art. The deletion plasmid is then cut at an appropriate restriction enzyme site(s) internal to the desired gene coding region, and the gene coding sequence or a part thereof is replaced with a selectable marker. Flanking DNA sequences from the locus of the gene to be deleted, e.g., between about 0.5 to 2.0 kb, remain on either side of the marker gene. An appropriate deletion plasmid will generally have unique restriction enzyme sites present to enable the fragment containing the deleted gene, including the flanking DNA sequences and the selectable markers gene, to be removed as a single linear piece.

Transformation, Expression and Culture of Host Cells

Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; and protoplast fusion. General transformation techniques are known in the art. See, e.g., Ausubel et al. (1987), supra, chapter 9; Sambrook et al. (2001), supra; and Campbell et al., *Curr. Genet.* 16: 53-56 (1989). The expression of heterologous protein in *Trichoderma* is described, for example, in U.S. Pat. Nos. 6,022,725; 6,268,328; Harkki et al., *Enzyme Microb. Technol.* 13: 227-233 (1991); Harkki et al., *BioTechnol.* 7: 596-603 (1989); EP 244,234; EP 215,594; and Nevalainen et al., "The molecular biology of *Trichoderma* and its application to the expression of both homologous and heterologous genes," in MOLECULAR INDUSTRIAL MYCOLOGY, Leong and Berka, eds., Marcel Dekker Inc., New York (1992), pp. 129-148. Reference is also made to Cao et al., *Science* 9: 991-1001 (2000) for transformation of *Aspergillus* strains. In one embodiment, genetically stable transformants are constructed with vector systems whereby the nucleic acid encoding a TrAA or variant thereof is stably integrated into a host cell chromosome. Transformants are then purified by known techniques.

In one nonlimiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on solid non-selective medium, e.g., a medium that lacks acetamide, harvesting spores from this culture medium and determining the percentage of these spores that subsequently germinate and grow on selective medium containing acetamide. Other methods known in the art may be used to select transformants.

In one specific embodiment, the preparation of *Trichoderma* sp. for transformation involves the preparation of protoplasts from fungal mycelia. See Campbell et al., *Curr. Genet.* 16: 53-56 (1989). In some embodiments, the mycelia are obtained from germinated vegetative spores. The mycelia are treated with an enzyme that digests the cell wall, resulting in protoplasts. The protoplasts are protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M, e.g., a 1.2 M solution of sorbitol can be used in the suspension medium.

Uptake of DNA into the host *Trichoderma* sp. strain is dependent upon the calcium ion concentration. Generally, between about 10-50 mM $CaCl_2$ is used in an uptake solution. Additional suitable compounds include a buffering system, such as TE buffer (10 mM Tris, pH 7.4; 1 mM EDTA) or 10 mM MOPS, pH 6.0 and polyethylene glycol. The polyethylene glycol is believed to fuse the cell membranes, thus permitting the contents of the medium to be delivered into the cytoplasm of the *Trichoderma* sp. strain. This fusion frequently leaves multiple copies of the plasmid DNA integrated into the host chromosome.

Usually transformation of *Trichoderma* sp. uses protoplasts or cells that have been subjected to a permeability treatment, typically at a density of $10^5$ to $10^7$/mL, particularly $2 \times 10^6$/mL. A volume of 100 µL of these protoplasts or cells in an appropriate solution (e.g., 1.2 M sorbitol and 50 mM $CaCl_2$) are mixed with the desired DNA. Generally, a high concentration of PEG is added to the uptake solution. From 0.1 to 1 volume of 25% PEG 4000 can be added to the protoplast suspension; however, it is useful to add about 0.25 volumes to the protoplast suspension. Additives, such as dimethyl sulfoxide, heparin, spermidine, potassium chloride and the like, may also be added to the uptake solution to facilitate transformation. Similar procedures are available for other fungal host cells. See, e.g., U.S. Pat. Nos. 6,022,725 and 6,268,328, both of which are incorporated by reference.

Generally, the mixture is then incubated at approximately 0° C. for a period of between 10 to 30 minutes. Additional PEG is then added to the mixture to enhance further the uptake of the desired gene or DNA sequence. The 25% PEG 4000 is generally added in volumes of 5 to 15 times the volume of the transformation mixture; however, greater and lesser volumes may be suitable. The 25% PEG 4000 is typically about 10 times the volume of the transformation mixture. After the PEG is added, the transformation mixture is incubated either at room temperature or on ice before the addition of a sorbitol and $CaCl_2$ solution. The protoplast suspension is then further added to molten aliquots of a growth medium. This growth medium permits the growth only of transformants.

Generally, cells are cultured in a standard medium containing physiological salts and nutrients. See, e.g., Pourquie et al., BIOCHEMISTRY AND GENETICS OF CELLULOSE DEGRADATION, Aubert et al., eds., Academic Press (1988), pp. 71-86; and Ilmen et al., *Appl. Environ. Microbiol.* 63: 1298-1306 (1997). Common commercially prepared media, e.g., Yeast Malt Extract (YM) broth, Luria Bertani (LB) broth, or Sabouraud Dextrose (SD) broth, also are suitable.

Standard culture conditions are suitable, e.g., cultures are incubated at approximately 28° C. in appropriate medium in shake cultures or fermenters until a desired level of expression of a TrAA or variant thereof is achieved. Preferred culture conditions for a given filamentous fungus are known in the art and are available, for example, from the American Type Culture Collection (ATCC) and Fungal Genetics Stock Center (FGSC). After fungal growth has been established, the cells are exposed to conditions effective to cause or permit the expression of a TrAA or a variant thereof.

3.4. Identification of TrAA Activity

To evaluate the expression of a TrAA or variant thereof in a host cell, assays can measure the expressed protein, corresponding mRNA, or maltogenic α-amylase activity. For example, suitable assays include Northern and Southern blotting, RT-PCR (reverse transcriptase polymerase chain reaction), and in situ hybridization, using an appropriately labeled hybridizing probe. Suitable assays also include measuring TrAA activity in a sample, for example, by assays directly measuring reducing sugars such as glucose in the culture media. For example, glucose concentration may be determined using glucose reagent kit No. 15-UV (Sigma Chemical Co.) or an instrument, such as Technicon Autoanalyzer. Glucoamylase activity may be assayed by the 3,5-dinitrosalicylic acid (DNS) method. See, Goto et al., *Biosci. Biotechnol. Biochem.* 58: 49-54 (1994).

Generally, the TrAA expressed by a *Trichoderma* or *Aspergillus* host will have a concentration in the culture medium of greater than 1 gram protein per liter (g/L), greater than 2 g/L, greater than 5 g/L, greater than 10 g/L, greater than 20 g/L, or greater than 25 g/L. In one embodiment, the TrAA or variant thereof expressed by a *Trichoderma* or *Aspergillus* host will be glycosylated, i.e., the TrAA or variant thereof will comprise a glycosyl moiety. In a particularly suitable embodiment, the glycosylation pattern will be the same as present in the wild-type TrAA.

3.5. Methods for Purifying TrAA

In general, a TrAA or variant thereof produced in cell culture is secreted into the medium and may be purified or isolated, e.g., by removing unwanted components from the cell culture medium. In some cases, a TrAA or variant thereof may be recovered from a cell lysate. In such cases, the enzyme is purified from the cells in which it was produced using techniques routinely employed by those of skill in the art. Examples include, but are not limited to, affinity chromatography, ion-exchange chromatographic methods, including high resolution ion-exchange, hydrophobic interaction chromatography, two-phase partitioning, ethanol precipitation, reverse phase HPLC, chromatography on silica or on a cation-exchange resin, such as DEAE, chromatofocusing, SDS-PAGE, ammonium sulfate precipitation, and gel filtration using Sephadex G-75, for example.

Fermentation

In some embodiments, fungal cells expressing a TrAA or variant thereof are grown under batch or continuous fermentation conditions. A classical batch fermentation is a closed system, where the composition of the medium is set at the beginning of the fermentation and is not altered during the fermentation. At the beginning of the fermentation, the medium is inoculated with the desired organism(s). In this method, fermentation is permitted to occur without the addition of any components to the system. Typically, a batch fermentation qualifies as a "batch" with respect to the addition of the carbon source, and attempts are often made to control factors such as pH and oxygen concentration. The metabolite and biomass compositions of the batch system change constantly up to the time the fermentation is stopped. Within batch cultures, cells progress through a static lag phase to a high growth log phase and finally to a stationary phase, where growth rate is diminished or halted. If untreated, cells in the stationary phase eventually die. In general, cells in log phase are responsible for the bulk of production of product.

A suitable variation on the standard batch system is the "fed-batch fermentation" system. In this variation of a typical batch system, the substrate is added in increments as the fermentation progresses. Fed-batch systems are useful when catabolite repression likely inhibits the metabolism of the cells and where it is desirable to have limited amounts of substrate in the medium. Measurement of the actual substrate concentration in fed-batch systems is difficult and is therefore estimated on the basis of the changes of measurable factors, such as pH, dissolved oxygen and the partial pressure of waste gases, such as $CO_2$. Batch and fed-batch fermentations are common and well known in the art.

Continuous fermentation is an open system where a defined fermentation medium is added continuously to a bioreactor, and an equal amount of conditioned medium is removed simultaneously for processing. Continuous fermentation generally maintains the cultures at a constant high density, where cells are primarily in log phase growth. Continuous fermentation allows for the modulation of one or more factors that affect cell growth and/or product concentration. For example, in one embodiment, a limiting nutrient, such as the carbon source or nitrogen source, is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

4. Compositions and Uses of TrAA and Variants Thereof

TrAA and its variants produced and purified by the methods described above are useful for a variety of industrial applications. In one embodiment, TrAA and its variants are useful in a starch conversion process, particularly in a saccharification process of a starch that has undergone liquefaction. The desired end-product may be any product that may be produced by the enzymatic conversion of the starch substrate. For example, the desired product may be a maltose-rich syrup, which can be used in other processes, such as the preparation of HFCS. The product alternatively may be a glucose-rich syrup, which can be used directly as a source of crystalline glucose, for example, or which can be converted into a number of other useful products, such as ascorbic acid intermediates (e.g., gluconate; 2-keto-L-gulonic acid; 5-ketogluconate; and 2,5-diketogluconate); 1,3-propanediol; aromatic amino acids (e.g., tyrosine, phenylalanine and tryptophan); organic acids (e.g., lactate, pyruvate, succinate, isocitrate, and oxaloacetate); amino acids (e.g., serine and glycine); antibiotics; enzymes; vitamins; and hormones.

In yet another embodiment, the starch conversion process may be a precursor to, or simultaneous with, a fermentation process designed to produce alcohol for fuel or drinking (i.e., potable alcohol). One skilled in the art is aware of various fermentation conditions that may be used in the production of these end-products. TrAA and variants thereof also are useful in compositions and methods of food preparation. These various uses of TrAA and its variants are described in more detail below.

Preparation of Starch Substrates

Those of general skill in the art are well aware of available methods that may be used to prepare starch substrates for use in the processes disclosed herein. For example, a useful starch substrate may be obtained from tubers, roots, stems, legumes, cereals or whole grain. More specifically, the granular starch may be obtained from corns, cobs, wheat, barley, rye, milo, sago, cassava, tapioca, *sorghum*, rice, peas, bean, banana, or potatoes. Corn contains about 60-68% starch; barley contains about 55-65% starch; millet contains about 75-80% starch; wheat contains about 60-65% starch; and polished rice contains 70-72% starch. Specifically contemplated starch substrates are corn starch and wheat starch. The starch from a grain may be ground or whole and includes corn solids, such as kernels, bran and/or cobs. The starch may be highly refined raw starch or feedstock from starch refinery processes. Various starches also are commercially available. For example, corn starch is available from Cerestar, Sigma, and Katayama Chemical Industry Co. (Japan); wheat starch is available from Sigma; sweet potato starch is available from Wako Pure Chemical Industry Co. (Japan); and potato starch is available from Nakaari Chemical Pharmaceutical Co. (Japan).

The starch substrate can be a crude starch from milled whole grain, which contains non-starch fractions, e.g., germ residues and fibers. Milling may comprise either wet milling or dry milling. In wet milling, whole grain is soaked in water or dilute acid to separate the grain into its component parts, e.g., starch, protein, germ, oil, kernel fibers. Wet milling efficiently separates the germ and meal (i.e., starch granules and protein) and is especially suitable for production of syrups. In dry milling, whole kernels are ground into a fine powder and processed without fractionating the grain into its component parts. Dry milled grain thus will comprise significant amounts of non-starch carbohydrate compounds, in addition to starch. Most ethanol comes from dry milling. Alternatively, the starch to be processed may be a highly refined starch quality, for example, at least 90%, at least 95%, at least 97%, or at least 99.5% pure.

Gelatinization and Liquefaction of Starch

As used herein, the term "liquefaction" or "liquefy" means a process by which starch is converted to less viscous and shorter chain dextrins. Generally, this process involves gelatinization of starch simultaneously with or followed by the addition of an α-amylase, although additional liquefaction-inducing enzymes optionally may be added. In some embodiments, the starch substrate prepared as described above is slurried with water. The starch slurry may contain starch as a weight percent of dry solids of about 10-55%, about 20-45%, about 30-45%, about 30-40%, or about 30-35%. α-Amylase (EC 3.2.1.1) may be added to the slurry, with a metering pump, for example. The α-amylase typically used for this application is a thermally stable, bacterial α-amylase, such as a *B. licheniformis* α-amylase. The α-amylase is usually supplied, for example, at about 1500 units per kg dry matter of starch. To optimize α-amylase stability and activity, the pH of the slurry is adjusted to about pH 5.5-6.5 and about 1 mM of calcium (about 40 ppm free calcium ions) typically is added. Other α-amylases may require different conditions. Bacterial α-amylase remaining in the slurry following liquefaction may be deactivated by lowering pH in a subsequent reaction step or by removing calcium from the slurry.

The slurry of starch plus the α-amylase may be pumped continuously through a jet cooker, which is steam heated to 105° C. Gelatinization occurs very rapidly under these conditions, and the enzymatic activity, combined with the significant shear forces, begins the hydrolysis of the starch substrate. The residence time in the jet cooker is very brief. The partly gelatinized starch may be passed into a series of holding tubes maintained at 100-105° C. and held for 5 min. to complete the gelatinization process. Hydrolysis to the required DE is completed in holding tanks at 90-100° C. or higher temperatures for about 1 to 2 hours. These tanks may contain baffles to discourage back mixing.

As used herein, the term "secondary liquefaction" refers the liquefaction step subsequent to primary liquefaction (heating to 90-100° C.), when the slurry is allowed to cool to room temperature. This cooling step can be 30 minutes to 180 minutes, e.g. 90 minutes to 120 minutes. As used herein, the term "minutes of secondary liquefaction" refers to the time that has elapsed from the start of secondary liquefaction to the time that the Dextrose Equivalent (DE) is measured.

The liquefied starch resulting from the process above typically contains about 98% oligosaccharides and about 2% maltose and 0.3% D-glucose. The liquefied starch typically is in the form of a slurry having about 10-50% ds; about 10-45%; about 15-40%; about 20-40%; about 25-40%; or about 25-35% ds.

Saccharification: Creation of Glucose or Maltose Syrups

The liquefied starch can be saccharified into either a glucose syrup or a maltose syrup using the TrAA and variants thereof, optionally in the presence of another enzyme(s). The exact composition of the products of saccharification depends on the combination of enzymes used, as well as the type of granular starch processed. Advantageously, the glucose syrup obtainable using the provided TrAA and variants thereof may contain D-glucose at about 96% w/w. The maximum amount of glucose that currently can be obtained under any set of saccharification conditions is about 95-97%. The glucose syrup may be used directly after concentration for the production of high-fructose syrups or for the production of crystalline glucose. Equally advantageously, the maltose syrup obtainable using the provided TrAA and variants thereof may contain maltose exceeding 60% w/w.

In general, TrAA or a variant thereof will be added to a slurry of a granular starch substrate in an amount of about 0.01-1 kg enzyme per metric ton of dry solids. In some embodiments, TrAA or a variant thereof is added at 0.1-5 kg/mt ds, or 0.3-1 kg/mt ds, or at about 0.5 kg/mt ds. The specific activity of the TrAA or variant thereof may be about 10,000-80,000 SKBU/g of enzyme, or about 15,000-60,000 SKBU/g, or about 15,000-30,000 SKBU/g.

TrAA or a variant thereof may be added to the slurry in the form of a purified enzyme. Alternatively, TrAA or a variant thereof may be added as an isolated enzyme solution. In one embodiment, TrAA or a variant thereof is added in the form of a cell extract produced from a culture of cells expressing the TrAA or variant thereof. In another embodiment, TrAA or a variant is added in the form of a host cell that expresses and secretes the TrAA or variant into the reaction medium, such that the enzyme is provided continuously into the reaction. In this embodiment, the host cell that expresses TrAA or a variant thereof may also express another enzyme that is used to catalyze saccharification in addition to TrAA or its variant. For example, a host cell, e.g., *Trichoderma reesei* or *Aspergillus niger*, may be engineered to co-express TrAA or a variant thereof and a glucoamylase, e.g., TrGA or HgGA. In one embodiment, the host cell is genetically modified so as not to express its endogenous glucoamylase.

Glucose Syrups

In one aspect, TrAA and its variants are used in a saccharification process to produce a glucose rich syrup. To produce a glucose syrup, TrAA or variants thereof typically are added with a glucoamylase (EC 3.2.1.3), e.g., AMG™ glucoamylase. As shown in TABLE 1, FIG. 1, and discussed in the examples below, the saccharification process catalyzed by TrAA or a variant thereof in the presence of a glucoamylase can yield glucose concentrations near or exceeding 97%. Advantageously, a maximum glucose concentration may be achieved in less time than if the reaction were catalyzed by a glucoamylase alone. In one embodiment, maximum glucose concentrations are achieved in 12 hours, 24 hours or 36 hours. See TABLE 2 and the associated text in the examples. Particularly advantageously, TrAA and its variants suppress the reverse reaction from glucose to malto-oligosaccharides, so that the maximum concentration of glucose is maintained over a longer time than in a conventional saccharification process. See TABLE 2. In some embodiments, the maximum concentration of glucose is maintained for about 12 hours or about 24 hours after the maximum concentration is reached.

One exemplary glucoamylase is *Trichoderma reesei* glucoamylase (TrGA) and variants thereof that possess superior specific activity and thermal stability. See U.S. Published Applications Nos. 2006/0094080, 2007/0004018, and 2007/0015266 (Genencor International, Inc.). Suitable variants of TrGA include those with glucoamylase activity and at least 80%, at least 90%, or at least 95% sequence identity to wildtpye TrGA. TrAA and its variants advantageously increase the yield of glucose produced in a saccharification process catalyzed by TrGA. Without the addition of TrAA or its variants, TrGA typically produces a solution of about 88% glucose at pH 4.3; however, when TrAA or its variants are added to the reaction, the mixture of TrAA and TrGA produces significantly a solution with a higher glucose concentration, e.g. 94%.

Alternatively, the glucoamylase may be another glucoamylase derived from plants, fungi, or bacteria. For example, the glucoamylases may be *Aspergillus niger* G1 or G2 glucoamylase or its variants (e.g., Boel et al., *EMBO J*. 3: 1097-1102 (1984), WO 92/00381 and WO 00/04136 (Novo Nordisk A/S)); and *A. awamori* glucoamylase (e.g., WO 84/02921 (Cetus Corp.)). Other contemplated *Aspergillus* glucoamylase include variants with enhanced thermal stability, e.g., G137A and G139A (Chen et al., *Prot. Eng*. 9: 499-505 (1996)); D257E and D293E/Q (Chen et al., *Prot. Eng*. 8: 575-582 (1995)); N182 (Chen et al., *Biochem. J*. 301: 275-281(1994)); A246C (Fierobe et al., *Biochemistry*, 35: 8698-8704 (1996)); and variants with Pro residues in positions A435 and S436 (Li et al., *Protein Eng*. 10: 1199-1204 (1997)). Other contemplated glucoamylases include *Talaromyces* glucoamylases, in particular derived from *T. emersonii* (e.g., WO 99/28448 (Novo Nordisk A/S), *T. leycettanus* (e.g., U.S. Pat. No. RE 32,153 (CPC International, Inc.)), *T. duponti*, or *T. thermophilus* (e.g., U.S. Pat. No. 4,587,215). Contemplated bacterial glucoamylases include glucoamylases from the genus *Clostridium*, in particular *C. thermoamylolyticum* (e.g., EP 135,138 (CPC International, Inc.) and *C. thermohydrosulfuricum* (e.g., WO 86/01831 (Michigan Biotechnology Institute)). Suitable glucoamylases include the glucoamylases derived from *Aspergillus oryzae*, such as a glucoamylase having 50%, 55%, 60%, 65%, 70%, 75%, 80%, 85%, or even 90% homology to the amino acid sequence shown in SEQ ID NO:2 in WO 00/04136 (Novo Nordisk A/S). Also suitable are commercial glucoamylases, such as AMG 200L; AMG 300 L; SAN™ SUPER and AMG™ E (from Novozymes); OPTIDEX® 300 (from Genencor International, Inc.); AMIGASE™ and AMIGASE™ PLUS (from DSM); G-ZYME® G900 (from Enzyme Bio-Systems); and G-ZYME® G990 ZR (*A. niger* glucoamylase with a low protease content). Glucoamylases typically are added in an amount of 0.02-2.0 GAU/g ds or 0.1-1.0 GAU/g ds, e.g., 0.2 GAU/g ds.

Other suitable enzymes that can be used with TrAA or its variants include a debranching enzyme, such as an isoamylase (EC 3.2.1.68). Debranching enzymes may be added in effective amounts well known to the person skilled in the art. A pullulanase (EC 3.2.1.41), e.g., Promozyme®, is also suitable. Pullulanase typically is added at 100 U/kg ds. Further suitable enzymes include proteases, such as fungal and bacterial proteases. Fungal proteases include those obtained from *Aspergillus*, such as *A. niger, A. awamori, A. oryzae; Mucor* (e.g., *M. miehei*); and *Rhizopus*. Other suitable enzymes include, but are not limited to, cellulases, hemicellulases, lipases and cutinases.

Whereas liquefaction is generally run as a continuous process, saccharification is often conducted as a batch process. Saccharification typically is most effective at temperatures of about 60° C. and a pH of about 4.0-4.5, e.g., pH 4.3, necessitating cooling and adjusting the pH of the liquefied starch. Saccharification may be performed, for example, at a temperature between about 40° C., about 50° C., or about 55° C. to about 60° C. Saccharification is normally conducted in stirred tanks, which may take several hours to fill or empty. Enzymes typically are added either at a fixed ratio to dried solids as the tanks are filled or added as a single dose at the commencement of the filling stage. A saccharification reaction to make a glucose syrup typically is run over about 24-72 hours, or 24-28 hours, or particularly 24 or fewer hours, e.g. 20-21 hours. When a maximum DE has been attained, the reaction is stopped by heating to 85° C. for 5 min., for example. Further incubation will result in a lower DE, eventually to about 90 DE, as accumulated glucose re-polymerizes to isomaltose with the approach of thermodynamic equilibrium. The final yield of glucose, as a percent of the total solubilized dry solids, may be at least about 85%, 90%, 91%, 92%, 93%, 94%, 95%, 96%, 97% or 98%. In one embodiment, the glucose is produced in a continuous process, and substantially all of the glucose is used to produce a fermentation product, such as ethanol.

4.3.2. Maltose Syrups

Figure 2:
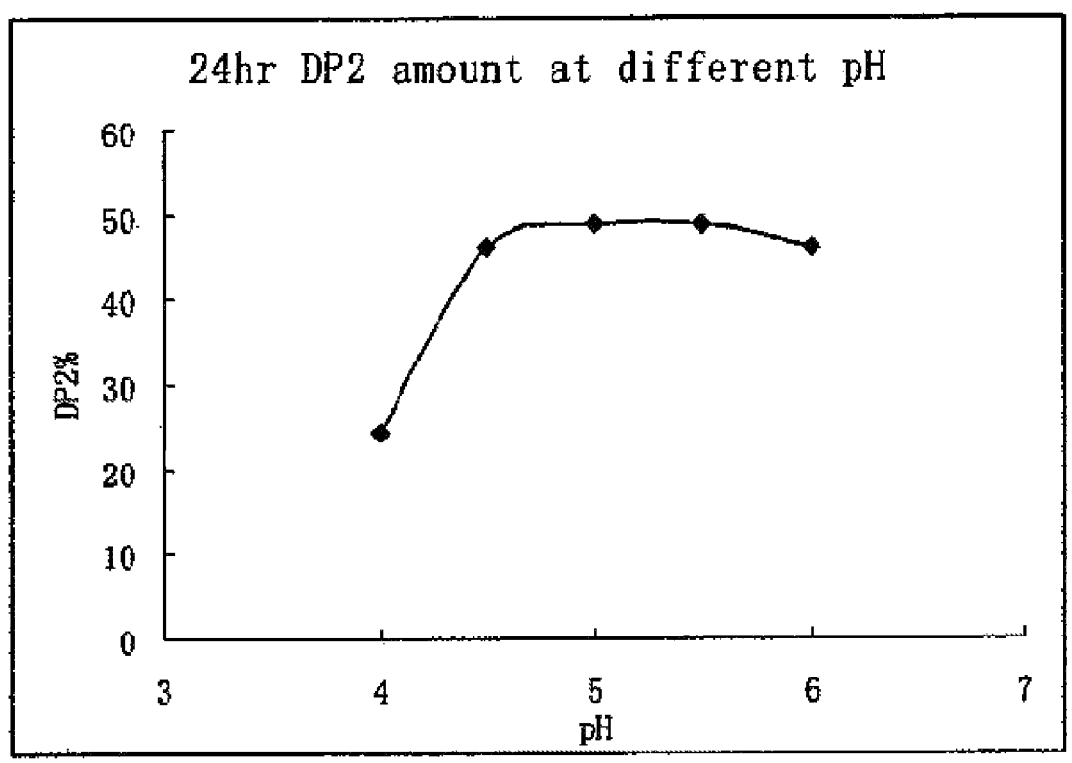
FIG. 2 depicts the ability of TrAA to catalyze the production of maltose at a low pH. The y-axis shows the weight percent of maltose (DP2) produced after 24 hours of a maltose production process catalyzed by 0.5 kg/mt ds TrAA at 55° C. The pH of the reaction is shown on the x-axis.

In another aspect, TrAA or a variant thereof is used in a process of producing a high-maltose syrup. Among the advantages offered by TrAA and its variants is the ability to use TrAA and its variants at relatively low pHs. A representative pH dependence of TrAA for the production of maltose (DP2) is depicted in FIG. 2. Because saccharification typically takes place under acidic conditions at elevated temperatures, e.g., 60° C., pH 4.3, the high activity of TrAA or its variants under these conditions advantageously allows TrAA or its variants to be used under conditions that are optimal for other enzymes, e.g., glucoamylases, used in saccharification.

High-maltose syrups produced with a TrAA or its variants have advantageous properties. The maltose concentration achieved using TrAA or its variants are comparable or higher than that achieved with conventional maltogenic enzymes, such as BBA or the fungal α-amylase Clarase® L. See TABLES 3 and 4 and FIG. 2. In one embodiment, the concentration of maltose reaches a percentage of dry solids of about 50% to about 62%. In another embodiment, the concentration of maltose reaches about 55%, about 60% or about 61% to about 62%. Further, the high-maltose syrup obtained using TrAA may contain glucose at a concentration of about 8-9%, whereas a conventional high-maltose syrup produced under comparable conditions, e.g., using Clarase® L, typically has a glucose concentration of about 4-5%. See TABLE 3. The relatively high yield of glucose advantageously gives the high-maltose syrup made using TrAA or its variants to be sweeter than high-maltose syrups produced using conventional enzymes.

TrAA or a variant thereof may catalyze the production of a high-maltose syrup by itself of in the presence of at least one other enzyme. A particularly suitable enzyme for use with TrAA or a variant thereof is pullulanase. The addition of a pullulanase significantly increases the yield of maltose, as shown in TABLE 5 and FIG. 3. The amount of pullulanase added may be about 0.1 kg/mt ds, about 0.25 kg/mt ds, or about 0.5 kg/mt ds. In one embodiment, the amount of pullulanase added to provide a maximum increase in maltose produced in the reaction. The data in TABLE 5 indicates that the effect of pullulanase on maltose formation is greatest when the concentration of pullulanase is about 0.25 kg/mt ds under the particular conditions used to produce maltose noted in the text accompanying TABLE 5 in the examples below.

Other enzymes suitable for use with TrAA or variants thereof include bacterial β-amylases, e.g., BBA, other fungal α-amylases, e.g., Clarase® L, or glucoamylase. Further suitable enzymes include proteases, such as fungal and bacterial proteases. Fungal proteases include those obtained from *Aspergillus*, such as *A. niger, A. awamori, A. oryzae; Mucor*, e.g., *M. miehei*; and *Rhizopus*. Other suitable enzymes include, but are not limited to, cellulases, hemicellulases, lipases, isoamylases, and cutinases.

β-amylases (EC 3.2.1.2) are exo-acting maltogenic amylases, which catalyze the hydrolysis of 1,4-α-glucosidic linkages into amylopectin and related glucose polymers, thereby releasing maltose. β-amylases have been isolated from various plants and microorganisms. See Fogarty et al., in PROGRESS IN INDUSTRIAL MICROBIOLOGY, Vol. 15, pp. 112-115 (1979). These β-amylases have optimum temperatures in the range from 40° C. to 65° C. and optimum pH in the range from about 4.5 to about 7.0. Contemplated β-amylases include, but are not limited to, β-amylases from barley Spezyme® BBA 1500, Spezyme® DBA, Optimalt™ ME, Optimalt™ BBA (Genencor International, Inc.); and Novozym™ WBA (Novozymes A/S).

HFCS Production and Fermentation

In one embodiment, the soluble starch hydrolysate produced by treatment with TrAA, variants thereof, or blends of enzymes comprising TrAA or its variants, is converted into high fructose starch-based syrup (HFSS), such as high fructose corn syrup (HFCS). This conversion can be achieved using a glucose isomerase, particularly a glucose isomerase immobilized on a solid support. The pH is increased to about 6.0 to about 8.0, e.g., pH 7.5, and $Ca^{2+}$ is removed by ion exchange. Suitable isomerases include Sweetzyme®, IT (Novozymes A/S); G-zyme® IMGI, and G-zyme® G993, Ketomax®, G-zyme® G993, G-zyme® G993 liquid, and GenSweet® IGI. Following isomerization, the mixture typically contains about 40-45% fructose, e.g., 42% fructose.

In another embodiment, the soluble starch hydrolysate, particularly a glucose rich syrup, is fermented by contacting the hydrolysate with a fermenting organism typically at a temperature around 32° C., such as from 30° C. to 35° C. Fermentation products include ethanol, citric acid, monosodium glutamate, gluconic acid, sodium gluconate, calcium gluconate, potassium gluconate, glucono delta-lactone, and sodium erythorbate. The saccharification and fermentation processes may be carried out as a simultaneous saccharification and fermentation (SSF) process. Fermentation optionally may comprise subsequent purification and recovery of ethanol. During the fermentation, the ethanol content of the broth or "beer" may reach at least about 8%, at least about 12%, or at about 16% ethanol. The broth may be distilled to produce enriched, e.g., 96% pure, solutions of ethanol. Further, $CO_2$ generated by fermentation may be collected with a $CO_2$ scrubber, compressed, and marketed for other uses, e.g., carbonating beverage or dry ice production. Solid waste from the fermentation process may be used as protein-rich products, e.g., livestock feed.

Ethanologenic microorganisms include yeast, such as Saccharomyces cerevisiae and bacteria, e.g., *Zymomonas mobilis*, expressing alcohol dehydrogenase and pyruvate decarboxylase. In some embodiments, the ethanologenic microorganism expresses xylose reductase and xylitol dehydrogenase, enzymes that convert xylose to xylulose. Commercial sources of yeast include RED STAR (Red Star); FERMIOL® (DSM Specialties) and SUPERSTART® (Altech).

In one embodiment, fungal cells expressing a heterologous glucoamylase and/or TrAA or its variants are grown under batch or continuous fermentation conditions. A classical batch fermentation is a closed system, where the composition of the medium is set at the beginning of the fermentation. That is, fermentation is permitted to occur without the addition of any components to the system. Within batch cultures, cells progress through a static lag phase to a high growth log phase and finally to a stationary phase where growth rate is diminished or halted. Generally, cells in log phase are responsible for the bulk of the heterologous production glucoamylase and/or TrAA or its variants.

A variation on this process is a "fed-batch fermentation" system, where the substrate is added in increments as the fermentation progresses. Fed-batch systems are useful when catabolite repression may inhibit the metabolism of the cells and where it is desirable to have limited amounts of substrate in the medium. The actual substrate concentration in fed-batch systems is estimated by the changes of measurable factors such as pH, dissolved oxygen and the partial pressure of waste gases, such as $CO_2$. Batch and fed-batch fermentations are common and well known in the art.

Continuous fermentation is an open system where a defined fermentation medium is added continuously to a bioreactor, and an equal amount of conditioned medium is removed simultaneously for processing. Continuous fermentation generally maintains the cultures at a constant high density where cells are primarily in log phase growth. Continuous fermentation permits modulation of cell growth and/or product concentration. For example, in one embodiment, a limiting nutrient such as the carbon source or nitrogen source is maintained at a fixed rate an all other parameters are allowed to moderate. Because growth is maintained at a steady state, cell loss due to medium being drawn off should be balanced against the cell growth rate in the fermentation. Methods of optimizing continuous fermentation processes and maximizing the rate of product formation are well known in the art of industrial microbiology.

Compositions and Methods for Baking and Food Preparation

For the commercial and home use of flour for baking and food production, it is important to maintain an appropriate level of α-amylase activity in the flour. A level of activity that is too high may result in a product that is sticky and/or doughy and therefore unmarketable. Flour with insufficient α-amylase activity may not contain enough sugar for proper yeast function, resulting in dry, crumbly bread, or baked products. Accordingly, a TrAA or variant thereof, by itself or in combination with another α-amylase(s), may be added to the flour to augment the level of endogenous α-amylase activity in flour. The TrAA or variant thereof in this embodiment can have a temperature optimum in the presence of starch in the ranges of 30-90° C., 40-80° C., 40-50° C., 45-65° C., or 50-60° C., for example. The pH optimum in a 1% solution of soluble starch may be between pH 4.5 to 6, for example.

Grains, such as barley, oats, wheat, as well as plant components, such as corn, hops, and rice, also are used for brewing, both in industry and for home brewing. The components used in brewing may be unmalted or may be malted, i.e., partially germinated, resulting in an increase in the levels of enzymes, including α-amylase. For successful brewing, adequate levels of α-amylase enzyme activity are necessary to ensure the appropriate levels of sugars for fermentation. A TrAA or variant thereof, by itself or in combination with another α-amylase(s), accordingly may be added to the components used for brewing.

As used herein, the term "flour" means milled or ground cereal grain. The term "flour" also may mean Sago or tuber products that have been ground or mashed. In some embodiments, flour may also contain components in addition to the milled or mashed cereal or plant matter. An example of an additional component, although not intended to be limiting, is a leavening agent. Cereal grains include wheat, oat, rye, and barley. Tuber products include tapioca flour, cassava flour, and custard powder. The term "flour" also includes ground corn flour, maize-meal, rice flour, whole-meal flour, self-rising flour, tapioca flour, cassava flour, ground rice, enriched flower, and custard powder.

As used herein, the term "stock" means grains and plant components that are crushed or broken. For example, barley used in beer production is a grain that has been coarsely ground or crushed to yield a consistency appropriate for producing a mash for fermentation. As used herein, the term "stock" includes any of the aforementioned types of plants and grains in crushed or coarsely ground forms. The methods described herein may be used to determine α-amylase activity levels in both flours and stock.

A TrAA or variant thereof further can be added alone or in a combination with other amylases to prevent or retard staling, i.e., crumb firming of baked products. The amount of anti-staling amylase will typically be in the range of 0.01-10 mg of enzyme protein per kg of flour, e.g., 0.5 mg/kg ds. Additional anti-staling amylases that can be used in combination with a TrAA or variant thereof include an endo-amylase, e.g., a bacterial endo-amylase from Bacillus. The additional amylase can be another maltogenic α-amylase (EC 3.2.1.133), e.g., from Bacillus. Novamyl® is an exemplary maltogenic α-amylase from B. stearothermophilus strain NCIB 11837 and is described in Christophersen et al., Starch 50: 39-45 (1997). Other examples of anti-staling endo-amylases include bacterial α-amylases derived from Bacillus, such as B. licheniformis or B. amyloliquefaciens. The anti-staling amylase may be an exo-amylase, such as β-amylase, e.g., from plant sources, such as soy bean, or from microbial sources, such as Bacillus.

The baking composition comprising a TrAA or variant thereof further can comprise a phospholipase. The phospholipase may have $A_1$ or $A_2$ activity to remove fatty acid from the phospholipids, forming a lysophospholipid. It may or may not have lipase activity, i.e., activity on triglyceride substrates. The phospholipase typically has a temperature optimum in the range of 30-90° C., e.g., 30-70° C. The added phospholipases can be of animal origin, for example, from pancreas, e.g., bovine or porcine pancreas, snake venom or bee venom. Alternatively, the phospholipase may be of microbial origin, e.g., from filamentous fungi, yeast or bacteria, such as the genus or species Aspergillus, A. niger; Dictyostelium, D. discoideum; Mucor, M. javanicus, M. mucedo, M. subtilissimus; Neurospora, N. crassa; Rhizomucor, R. pusillus; Rhizopus, R. arrhizus, R. japonicus, R. stolonifer; Sclerotinia, S. libertiana; Trichophyton, T. rubrum; Whetzelinia, W. sclerotiorum; Bacillus, B. megaterium, B. subtilis; Citrobacter, C. freundii; Enterobacter, E. aerogenes, E. cloacae; Edwardsiella, E. tarda; Etwinia, E. herbicola; Escherichia, E. coli; Klebsiella, K. pneumoniae; Proteus, P. vulgaris; Providencia, P. stuartii; Salmonella, S. typhimurium; Serratia, S. liquefasciens, S. marcescens; Shigella, S. flexneri; Streptomyces, S. violeceoruber; Yersinia, Y. enterocolitica; Fusarium, F. oxysporum, strain DSM 2672), for example.

The phospholipase is added in an amount that improves the softness of the bread during the initial period after baking, particularly the first 24 hours. The amount of phospholipase will typically be in the range of 0.01-10 mg of enzyme protein per kg of flour, e.g., 0.1-5 mg/kg. That is, phospholipase activity generally will be in the range of 20-1000 Lipase Unit (LU)/kg of flour, where a Lipase Unit is defined as the amount of enzyme required to release 1 μmol butyric acid per minute at 30° C., pH 7.0, with gum arabic as emulsifier and tributyrin as substrate.

Compositions of dough generally comprise wheat meal or wheat flour and/or other types of meal, flour or starch such as corn flour, cornstarch, rye meal, rye flour, oat flour, oatmeal, soy flour, sorghum meal, sorghum flour, potato meal, potato flour or potato starch. The dough may be fresh, frozen or par-baked. The dough can be a leavened dough or a dough to be subjected to leavening. The dough may be leavened in various ways, such as by adding chemical leavening agents, e.g., sodium bicarbonate or by adding a leaven, i.e., fermenting dough. Dough also may be leavened by adding a suitable yeast culture, such as a culture of *Saccharomyces cerevisiae* (baker's yeast), e.g., a commercially available strain of *S. cerevisiae*.

The dough may also comprise other conventional dough ingredients, e.g., proteins, such as milk powder, gluten, and soy; eggs (e.g., whole eggs, egg yolks or egg whites); an oxidant, such as ascorbic acid, potassium bromate, potassium iodate, azodicarbonamide (ADA) or ammonium persulfate; an amino acid such as L-cysteine; a sugar; or a salt, such as sodium chloride, calcium acetate, sodium sulfate or calcium sulfate. The dough further may comprise fat, e.g., triglyceride, such as granulated fat or shortening. The dough further may comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, or lysolecithin. In particular, the dough can be made without addition of emulsifiers.

Optionally, an additional enzyme may be used together with the anti-staling amylase and the phospholipase. The additional enzyme may be a second amylase, such as an amyloglucosidase, a β-amylase, a cyclodextrin glucanotransferase, or the additional enzyme may be a peptidase, in particular an exopeptidase, a transglutaminase, a lipase, a cellulase, a hemicellulase, in particular a pentosanase, such as xylanase, a protease, a protein disulfide isomerase, e.g., a protein disulfide isomerase as disclosed in WO 95/00636, for example, a glycosyltransferase, a branching enzyme (1,4-α-glucan branching enzyme), a 4-α-glucanotransferase (dextrin glycosyltransferase) or an oxidoreductase, e.g., a peroxidase, a laccase, a glucose oxidase, a pyranose oxidase, a lipooxygenase, an L-amino acid oxidase or a carbohydrate oxidase. The additional enzyme(s) may be of any origin, including mammalian and plant, and particularly of microbial (bacterial, yeast or fungal) origin and may be obtained by techniques conventionally used in the art.

The xylanase is typically of microbial origin, e.g., derived from a bacterium or fungus, such as a strain of *Aspergillus*, in particular of *A. aculeatus, A. niger* (cf. WO 91/19782), *A. awamori* (e.g., WO 91/18977), or *A. tubingensis* (e.g., WO 92/01793); from a strain of *Trichoderma*, e.g., *T. reesei*, or from a strain of *Humicola*, e.g., *H. insolens* (e.g., WO 92/17573). Pentopan® and Novozym 384® are commercially available xylanase preparations produced from *Trichoderma reesei*. The amyloglucosidase may be an *A. niger* amyloglucosidase (such as AMG®). Other useful amylase products include Grindamyl® A 1000 or A 5000 (available from Grindsted Products, Denmark) and Amylase® H or Amylase® P (available from Gist-Brocades, The Netherlands). The glucose oxidase may be a fungal glucose oxidase, in particular an *Aspergillus niger* glucose oxidase (such as Gluzyme®). An exemplary protease is Neutrase®. An exemplary lipase can be derived from strains of *Thermomyces (Humicola), Rhizomucor, Candida, Aspergillus, Rhizopus*, or *Pseudomonas*, in particular from *Thermomyces lanuginosus (Humicola lanuginosa), Rhizomucor miehei, Candida antarctica, Aspergillus niger, Rhizopus delemar* or *Rhizopus arrhizus*, or *Pseudomonas cepacia*. In specific embodiments, the lipase may be Lipase A or Lipase B derived from *Candida antarctica* as described in WO 88/02775, for example, or the lipase may be derived from *Rhizomucor miehei* as described in EP 238,023, for example, or *Humicola lanuginosa*, described in EP 305,216, for example, or *Pseudomonas cepacia* as described in EP 214,761 and WO 89/01032, for example.

The process may be used for any kind of baked product prepared from dough, either of a soft or a crisp character, either of a white, light or dark type. Examples are bread, particularly white, whole-meal or rye bread, typically in the form of loaves or rolls, such as, but not limited to, French baguette-type bread, pita bread, tortillas, cakes, pancakes, biscuits, cookies, pie crusts, crisp bread, steamed bread, pizza and the like.

In another embodiment, a TrAA or variant thereof may be used in a pre-mix, comprising flour together with an anti-staling amylase, a phospholipase and a phospholipid. The pre-mix may contain other dough-improving and/or bread-improving additives, e.g., any of the additives, including enzymes, mentioned above. In one aspect, the TrAA or variant thereof is a component of an enzyme preparation comprising an anti-staling amylase and a phospholipase, for use as a baking additive.

The enzyme preparation is optionally in the form of a granulate or agglomerated powder. The preparation can have a narrow particle size distribution with more than 95% (by weight) of the particles in the range from 25 to 500 μm. Granulates and agglomerated powders may be prepared by conventional methods, e.g., by spraying the TrAA or variant thereof onto a carrier in a fluid-bed granulator. The carrier may consist of particulate cores having a suitable particle size. The carrier may be soluble or insoluble, e.g., a salt (such as NaCl or sodium sulfate), a sugar (such as sucrose or lactose), a sugar alcohol (such as sorbitol), starch, rice, corn grits, or soy.

Another aspect contemplates the enveloping of particles comprising a TrAA or variant thereof, i.e., α-amylase particles. To prepare the enveloped α-amylase particles, the enzyme is contacted with a food grade lipid in sufficient quantity to suspend all of the α-amylase particles. Food grade lipids, as used herein, may be any naturally organic compound that is insoluble in water but is soluble in non-polar organic solvents such as hydrocarbon or diethyl ether. Suitable food grade lipids include, but are not limited to, triglycerides either in the form of fats or oils that are either saturated or unsaturated. Examples of fatty acids and combinations thereof which make up the saturated triglycerides include, but are not limited to, butyric (derived from milk fat), palmitic (derived from animal and plant fat), and/or stearic (derived from animal and plant fat). Examples of fatty acids and combinations thereof which make up the unsaturated triglycerides include, but are not limited to, palmitoleic (derived from animal and plant fat), oleic (derived from animal and plant fat), linoleic (derived from plant oils), and/or linolenic (derived from linseed oil). Other suitable food grade lipids include, but are not limited to, monoglycerides and diglycerides derived from the triglycerides discussed above, phospholipids and glycolipids.

The food grade lipid, particularly in the liquid form, is contacted with a powdered form of the α-amylase particles in such a fashion that the lipid material covers at least a portion of the surface of at least a majority, e.g., 100% of the α-amylase particles. Thus, each α-amylase particle is individually enveloped in a lipid. For example, all or substantially all of the α-amylase particles are provided with a thin, continuous, enveloping film of lipid. This can be accomplished by first pouring a quantity of lipid into a container, and then slurrying the α-amylase particles so that the lipid thoroughly wets the surface of each α-amylase particle. After a short period of stirring, the enveloped α-amylase particles, carrying a substantial amount of the lipids on their surfaces, are recovered. The thickness of the coating so applied to the particles of α-amylase can be controlled by selection of the type of lipid used and by repeating the operation in order to build up a thicker film, when desired.

The storing, handling and incorporation of the loaded delivery vehicle can be accomplished by means of a packaged mix. The packaged mix can comprise the enveloped α-amylase. However, the packaged mix may further contain additional ingredients as required by the manufacturer or baker. After the enveloped α-amylase has been incorporated into the dough, the baker continues through the normal production process for that product.

The advantages of enveloping the α-amylase particles are two-fold. First, the food grade lipid protects the enzyme from thermal denaturation during the baking process for those enzymes that are heat labile. Consequently, while the α-amylase is stabilized and protected during the proving and baking stages, it is released from the protective coating in the final baked good product, where it hydrolyzes the glucosidic linkages in polyglucans. The loaded delivery vehicle also provides a sustained release of the active enzyme into the baked good. That is, following the baking process, active α-amylase is continually released from the protective coating at a rate that counteracts, and therefore reduces the rate of, staling mechanisms.

In general, the amount of lipid applied to the α-amylase particles can vary from a few percent of the total weight of the α-amylase to many times that weight, depending upon the nature of the lipid, the manner in which it is applied to the α-amylase particles, the composition of the dough mixture to be treated, and the severity of the dough-mixing operation involved.

The loaded delivery vehicle, i.e., the lipid-enveloped enzyme, is added to the ingredients used to prepare a baked good in an effective amount to extend the shelf-life of the baked good. The baker computes the amount of enveloped α-amylase, prepared as discussed above, that will be required to achieve the desired anti-staling effect. The amount of the enveloped α-amylase required is calculated based on the concentration of enzyme enveloped and on the proportion of α-amylase to flour specified. A wide range of concentrations has been found to be effective, although, as has been discussed, observable improvements in anti-staling do not correspond linearly with the α-amylase concentration, but above certain minimal levels, large increases in α-amylase concentration produce little additional improvement. The α-amylase concentration actually used in a particular bakery production could be much higher than the minimum necessary in order to provide the baker with some insurance against inadvertent under-measurement errors by the baker. The lower limit of enzyme concentration is determined by the minimum anti-staling effect the baker wishes to achieve.

A method of preparing a baked good may comprise: a) preparing lipid-coated α-amylase particles, where substantially all of the α-amylase particles are coated; b) mixing a dough containing flour; c) adding the lipid-coated α-amylase to the dough before the mixing is complete and terminating the mixing before the lipid coating is removed from the α-amylase; d) proofing the dough; and e) baking the dough to provide the baked good, where the α-amylase is inactive during the mixing, proofing and baking stages and is active in the baked good.

The enveloped α-amylase can be added to the dough during the mix cycle, e.g., near the end of the mix cycle. The enveloped α-amylase is added at a point in the mixing stage that allows sufficient distribution of the enveloped α-amylase throughout the dough; however, the mixing stage is terminated before the protective coating becomes stripped from the α-amylase particle(s). Depending on the type and volume of dough, and mixer action and speed, anywhere from one to six minutes or more might be required to mix the enveloped α-amylase into the dough, but two to four minutes is average. Thus, several variables may determine the precise procedure. First, the quantity of enveloped α-amylase should have a total volume sufficient to allow the enveloped α-amylase to be spread throughout the dough mix. If the preparation of enveloped α-amylase is highly concentrated, additional oil may need to be added to the pre-mix before the enveloped α-amylase is added to the dough. Recipes and production processes may require specific modifications; however, good results generally can be achieved when 25% of the oil specified in a bread dough formula is held out of the dough and is used as a carrier for a concentrated enveloped α-amylase when added near the end of the mix cycle. In bread or other baked goods, particularly those having a low fat content, e.g., French-style breads, an enveloped α-amylase mixture of approximately 1% of the dry flour weight is sufficient to admix the enveloped α-amylase properly with the dough. The range of suitable percentages is wide and depends on the formula, finished product, and production methodology requirements of the individual baker. Second, the enveloped α-amylase suspension should be added to the mix with sufficient time for complete mixture into the dough, but not for such a time that excessive mechanical action strips the protective lipid coating from the enveloped α-amylase particles.

7. Textile Desizing Compositions and Use

Also contemplated are compositions and methods of treating fabrics (e.g., to desize a textile) using a TrAA or a variant thereof. Fabric-treating methods are well known in the art (see, e.g., U.S. Pat. No. 6,077,316). For example, in one aspect, the feel and appearance of a fabric is improved by a method comprising contacting the fabric with a TrAA or a variant thereof in a solution. In one aspect, the fabric is treated with the solution under pressure.

In one aspect, a TrAA or a variant thereof is applied during or after the weaving of a textile, or during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. A TrAA or a variant thereof can be applied during or after the weaving to remove these sizing starch or starch derivatives. After weaving, a TrAA or a variant thereof can be used to remove the size coating before further processing the fabric to ensure a homogeneous and wash-proof result.

A TrAA or a variant thereof can be used alone or with other desizing chemical reagents and/or desizing enzymes to desize fabrics, including cotton-containing fabrics, as detergent additives, e.g., in aqueous compositions. A TrAA or a variant thereof also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of amylolytic enzymes to provide softness to the fabric and make the cotton more accessible to the subsequent enzymatic finishing steps. A TrAA or a variant thereof can be used in methods of finishing denim garments (e.g., a "bio-stoning process"), enzymatic desizing and providing softness to fabrics, and/or finishing process.

It will be apparent to those skilled in the art that various modifications and variation can be made to the compositions and methods of using the same without departing from the spirit or scope of the intended use. Thus, it is the modifications and variations provided they come within the scope of the appended claims and their equivalents.

EXAMPLES

Example 1

1.1 Cloning of the TrAA Gene

Chromosomal DNA of *T. reesei* QM6a was isolated from a mycelial mass of a liquid culture in Potato Dextrose Broth (Difco™ Cat. No. 254920) using the BIO101 Fast Prep® System according to the method described by the supplier (Qbiogene, Inc., Irvine, Calif.). The DNA was purified using a Quick Spin column (Qiagen, Inc., Valencia, Calif.; Cat. No. 28106). The TrAA gene was isolated using primers with TrAA-specific sequences, a forward primer NSP331 (SEQ ID NO:6: ATGAAGCTCCGGTACGCTCTCC) and a reverse primer NSP332 (SEQ ID NO:7: TCACGAAGACAGCAA-GACAATGGGC) designed according to the predicted nucleotide sequence in the *Trichoderma reesei* genome database of the United States Department of Energy Joint Genome Institute. The primers were flanked at the 5' end by Gateway® attB sequences (Invitrogen Corp., Carlsbad, Calif.). *T. reesei* QM6a chromosomal DNA was used as template.

The PCR mix contained the following components: 4 µL forward primer (10 µM); 4 µL reverse primer (10 µM); 1 µL template DNA (500 ng/µL); 2 µL dNTP mix (10 mM); 10 µL 10× Cx buffer; and 0.5 µL PfuTurbo® Cx Hotstart DNA polymerase (Stratagene, La Jolla, Calif.; Cat. No. 600410). Deionized water was added up to a total volume of 100 µL. The PCR protocol was as follows: Initial denaturation for 30 sec at 98° C., denaturation, annealing, and extension in 30 cycles of 10 sec at 98° C.; 30 sec at 68° C.; 45 sec at 72° C., respectively, and a final extension step of 10 min at 72° C.

The PCR fragments were analyzed by electrophoresis in 1% agarose. Fragments of the expected size were isolated using the Gel-Extraction Purification Kit (Qiagen Cat. No. 28706). The PCR fragments were cloned into the Gateway® Entry vector pDONR201 and transformed into *E. coli* DH5α Max Efficiency cells (Invitrogen Cat. No. 18258012). The nucleotide sequence of the inserted DNA was determined, from which the genomic DNA sequence of the TrAA gene was deduced (SEQ ID NO:1).

1.2 Transformation of *T. reesei* and Fermentation/Expression of TrAA

Vector DNA containing the TrAA gene was recombined into the *T. reesei* expression vector pTrex3g, which is described in detail in WO 2006/060062. The resulting expression vector was transformed into a *T. reesei* host strain derived from RL-P37 having various gene deletions (Δcbh1, Δcbh2, Δegl1, Δegl2, i.e., "quad-deleted"; see WO 92/06184 and WO 05/001036) using particle bombardment by the PDS-1000/Helium System (Bio-Rad Laboratories, Inc., Hercules, Calif.; Cat. No. 165-02257). The protocol is outlined below, and reference is made to examples 6 and 11 of WO 05/001036.

A suspension of spores (approximately $5 \times 10^8$ spores/mL) from a quad-deleted strain of *T. reesei* was prepared. A spore suspension of 100-200 µL was spread onto the center of plates of Minimal Medium (MM) acetamide medium. MM acetamide medium is 0.6 g/L acetamide; 1.68 g/L CsCl; 20 g/L glucose; 20 g/L $KH_2PO_4$; 0.6 g/L $CaCl_2.2H_2O$; trace elements solution; 20 g/L Noble agar; pH 5.5. A 1000× trace elements stock solution contained 5.0 g/L $FeSO_4.7H_2O$; 1.6 g/L $MnSO_4.H_2O$; 1.4 g/L $ZnSO_4.7H_2O$; and 1.0 g/L $CoCl_2.6H_2O$. The spore suspension was allowed to dry on the surface of the MM acetamide medium.

Transformation followed the manufacturer's instruction. Briefly, 60 mg of M10 tungsten particles were placed in a microcentrifuge tube. 1 mL of ethanol was added, and the solution was allowed to stand for 15 sec. The particles were centrifuged at 15,000 rpm for 15 sec. The ethanol was removed, and the particles were washed three times with sterile $dH_2O$ before 250 µL of 50% (v/v) sterile glycerol was added. 25 µL of the tungsten particle suspension were placed into a microtrifuge tube. The following solutions were then added with continuous vortexing: 5 µL (100-200 ng/µL) of plasmid DNA, 25 µL 2.5 M $CaCl_2$, and 10 µL 0.1M spermidine. The particles were centrifuged for 3 sec. The supernatant was removed, and the particles were washed with 200 µL 100% ethanol and centrifuged for 3 sec. The supernatant was removed, 24 µL 100% ethanol was added and mixed by pipetting, then 8 µL aliquots of particles were removed and placed onto the center of macrocarrier disks in a desiccator. Once the tungsten/DNA solution were dry, the macrocarrier disks were placed in a bombardment chamber along with the plate of MM acetamide with spores, and the bombardment process was performed according to the manufacturer's instructions. After bombardment of the plated spores with the tungsten/DNA particles, the plates were incubated at 30° C. Transformed colonies were transferred to fresh plates of MM acetamide medium and incubated at 30° C.

1.3 Demonstration of α-Amylase Activity of Expressed TrAA

After 5 days of growth on MM acetamide plates, transformants displaying stable morphology were inoculated into 250 mL shake flasks containing 30 mL Proflo medium. Proflo medium contained 30 g/L α-lactose; 6.5 g/L $(NH_4)_2SO_4$; 2 g/L $KH_2PO_4$; 0.3 g/L $MgSO_4.7H_2O$; 0.2 g/L $CaCl_2$; trace element solution; 2 mL/L 10% Tween 80; 22.5 g/L ProFlo cottonseed flour (Traders Protein, Memphis, Tenn.); and 0.72 g/L $CaCO_3$. After two days growth at 28° C. with shaking at 140 rpm, 10% of the Proflo culture was transferred to a 250 mL shake flask containing 30 mL of Lactose Defined Media. The composition of the Lactose Defined Media is 5 g/L $(NH_4)_2SO_4$; 33 g/L PIPPS buffer; 9 g/L casamino acids; 4.5 g/L $KH_2SO_4$; 1.0 g/L $MgSO_4.7H_2O$; 5 mL/L Mazu DF60-P antifoam (Mazur Chemicals, Ill.); trace element solution; pH 5.5. After sterilization, 40 mL/L 40% (w/v) lactose solution was added to the medium. The Lactose Defined Medium shake flasks were incubated at 28° C., 140 rpm for 4-5 days.

Mycelia were removed by centrifugation, and the supernatant was analyzed for total protein (BCA Protein Assay Kit, Pierce CA; Cat. No. 23225). α-Amylase activity was assayed using the Ceralpha reagent (benzylidene-blocked p-nitrophenyl maltoheptaoside) as a substrate (Megazyme International Ireland, Ltd., Wicklow, Ireland; Cat. No. K-CERA).

Figure 5:
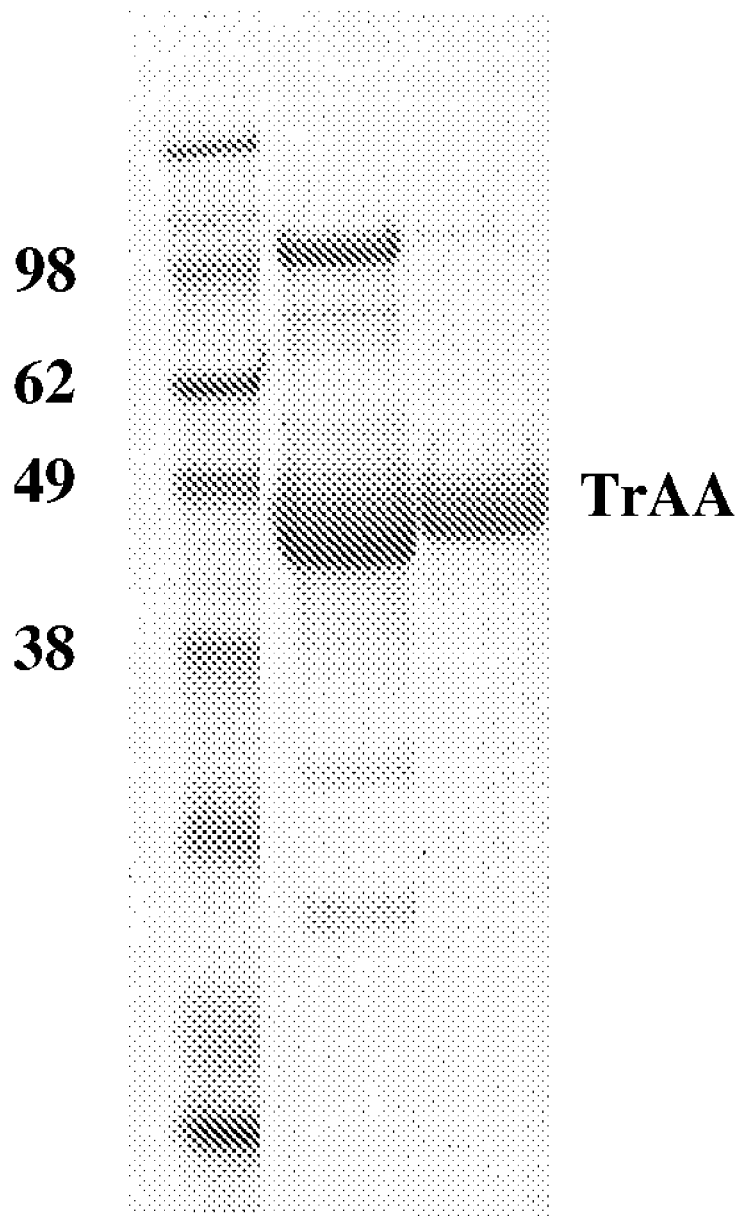
FIG. 5 shows SDS-PAGE-resolved proteins from an aliquot of cultured cells expressing TrAA (lane 1) or from purified TrAA (lane 2). Molecular weight markers at shown in lane M.

Samples of the culture supernatant were mixed with an appropriate volume of 2× sample loading buffer with reducing agent, and protein were resolved by sodium dodecyl sulfate-polyacrylamide gel electrophoresis (SDS-PAGE) using NUPAGE® Novex 10% Bis-Tris Gel with MES SDS Running Buffer. Proteins were stained with SimplyBlue™ SafeStain (Invitrogen, Carlsbad, Calif.). The protein staining pattern from a crude sample of culture supernatant is shown in FIG. 5, lane 1. It is apparent that the host cells express relatively high amounts of a protein with an apparent molecular weight of about 47 kDa, as determined by comparison with molecular weight markers in lane M. This TrAA is estimated to be about 89% pure.

1.4 Biochemical Characterization of the TrAA Gene Product

TrAA expressing transformants were grown in a 3 L culture. The host cell secreted TrAA into the culture at a concentration of about 15-20 g/L. The culture filtrate was concentrated using an ultrafiltration unit with a molecular weight limit of 10,000 Da (Pall Corp., Omega™ Membrane, Cat. No. OS010c10). The crude enzyme preparation was purified using an ÄKTA explorer 100 FPLC System (Amersham Biosciences, Piscataway, N.J.). A HiPrep 16/10 FF Q-Sepharose column (Amersham BioSciences, Cat. No. 17-5190-01) was equilibrated with 25 mM Tris, pH 6.0, and the protein was eluted from the column with 100 mM NaCl, 25 mM Tris, pH 6.0. A second affinity chromatography step was performed using Cbind 200 resin (Novagen Cat. No. 701212-3) and 50 mM Tris pH 7.0 containing 500 mM NaCl as elution buffer. Following this affinity purification, the TrAA may be concentrated again by ultrafiltration as described above. The purified TrAA was analyzed by SDS-PAGE, and the results are shown in FIG. 5, lane 2. The TrAA was estimated to be about 98% pure.

Figure 6A:
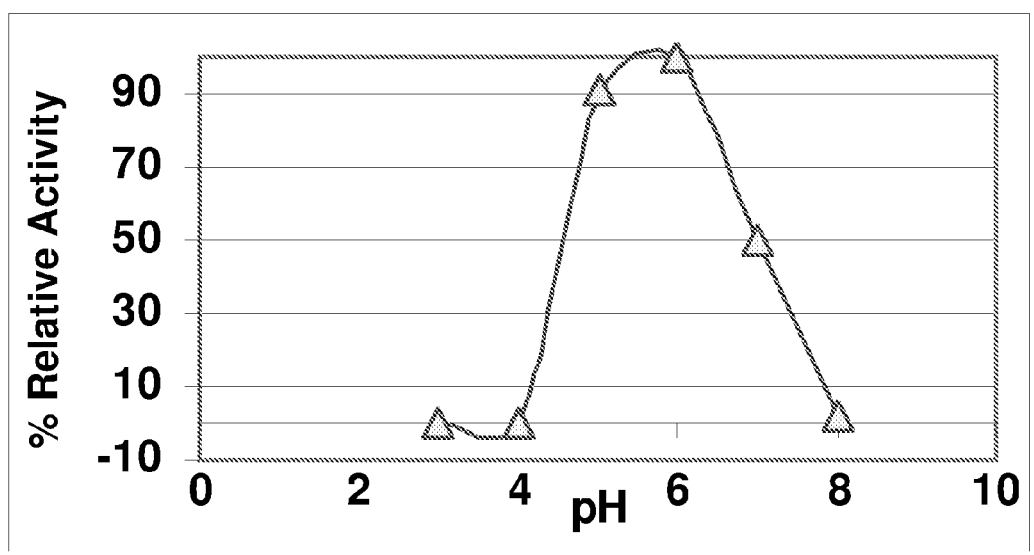
FIG. 6A shows relative α-amylase activity (in arbitrary units) of purified TrAA as a function of pH, using Ceralpha reagent (Megazyme International Ireland, Ltd., Wicklow, Ireland; Cat. No. K-CERA) as a substrate.
Figure 6B:
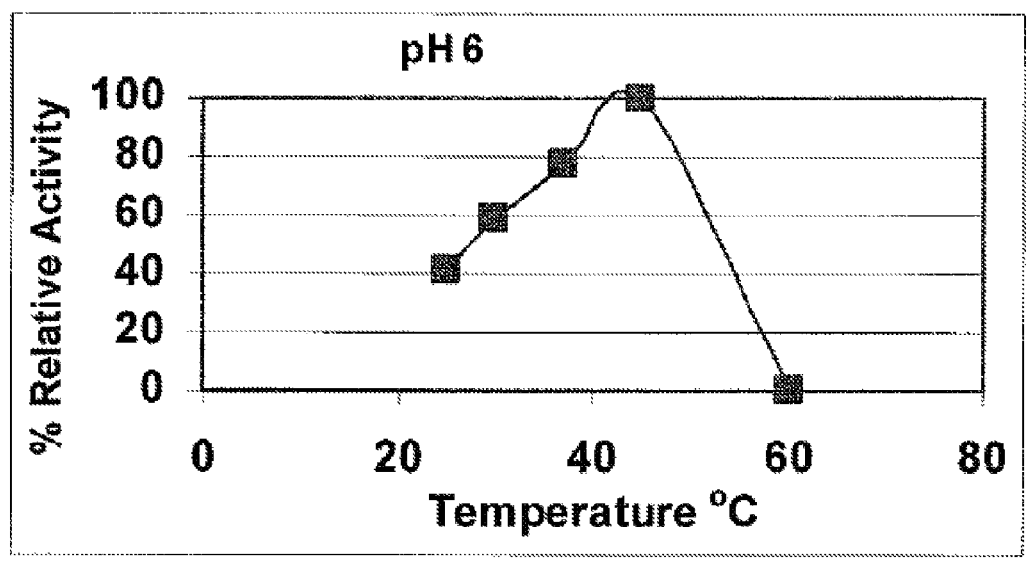
FIG. 6B shows relative α-amylase activity (in arbitrary units) of purified TrAA as a function of temperature, using the same artificial substrate.

The pH and temperature profiles of the α-amylase activity of the gene product were determined using Ceralpha reagent (Megazyme International Ireland, Ltd., Wicklow, Ireland; Cat. No. K-CERA) as a substrate. As shown in FIG. 6A, TrAA demonstrates an optimum pH of about pH 5-6, and as shown in FIG. 6B, TrAA demonstrates a temperature optimum of about 42° C. under the tested conditions.

Example 2

TrAA is useful for increasing the yield of glucose in a saccharification reaction catalyzed by a glucoamylase at a low pH. TrAA (Lot No. GCI2004017/018-UF) was purified as described in section 1.3 of Example 1. Glucoamylase was from GA-L, Lot No. 901-04290-001 (Genencor International, Inc.), which had a activity of 385 GAU/g. The substrate consisted of a liquefied starch substrate prepared as follows: 745 g raw corn starch was diluted with water to create a slurry of 32% w/w ds. The thermostable bacterial α-amylase Spezyme® Ethyl (Genencor International, Inc.), Lot No. 107-04107-001, was added to a concentration of 0.3 kg/mt ds, and the solution was liquefied at 92° C. for 25 min. An iodine test was performed to measure the remaining concentration of starch using procedures well known in the art.

The liquefied starch was cooled to 60° C. and the pH was adjusted to 4.2 with 20% v/v sulfuric acid. TrAA and Optimax® 4060 were added at the concentrations indicated below, and the reaction was run for 30 hours at 60° C. At the end of the reaction, DPn produced by the reaction were determined using HPLC, following dilution of sample 1:40 with HPLC-grade water and filtration of the samples through a 0.45 micron filter. For HPLC analysis, 20 µL samples were injected onto a Phenomenex Rezex ROA-Organic Acid (H+) column and resolved in a 16 min. run in a mobile phase of HPLC-grade water at 60° C. Products (DPn) in the eluant were measured by the change in refractive index.

TABLE 1 shows the DPn obtained from a representative reaction; FIG. 1 depicts DP1 production as a function of enzyme concentrations used in this experiment. As can be seen, TrAA in the presence of a glucoamylase produces a glucose-rich syrup having a higher glucose concentration than a glucoamylase by itself.

TABLE 1

| GA | TrAA | Time (hr) | DP1 | DP2 | DP3 | DP4+ |
|---|---|---|---|---|---|---|
| 0.6 kg/mt ds | None | 30 | 95.7 | 1.7 | 0.2 | 2.5 |
| 0.6 kg/mt ds | 0.06 kg/mt ds | 30 | 96.7 | 1.7 | 0.1 | 1.5 |
| 0.6 kg/mt ds | 0.12 kg/mt ds | 30 | 96.7 | 1.8 | 0.2 | 1.3 |
| 0.6 kg/mt ds | 0.18 kg/mt ds | 30 | 97.0 | 1.8 | 0.2 | 1.1 |
| 0.6 kg/mt ds | 0.3 kg/mt ds | 30 | 97.2 | 1.8 | 0.2 | 0.8 |

Example 3

A saccharification reaction catalyzed by TrAA and a glucoamylase reaches a higher level of glucose in a shorter time than a reaction catalyzed only by a glucoamylase. Liquefied raw corn starch was prepared as described in Example 2 as a 32% ds slurry. The liquefied starch was cooled to 60° C. and the pH was adjusted to 4.2 before the addition of enzymes at the concentrations indicated in TABLE 2. TrAA (Lot No. GCI2004017/018-UF) was prepared as described in section 1.3 of Example 1. Glucoamylase was provided as GA-L (Lot No. 901-04290-001) at 385 GAU/g. DPn were measured at the end of the reaction as indicated in Example 2 above.

TABLE 2

| GA | TrAA | Time (hr) | DP1 | DP2 | DP3 | DP4+ |
|---|---|---|---|---|---|---|
| 1 kg/mt ds | None | 21 | 93.9 | 2.5 | 0.3 | 3.3 |
| | | 24 | 94.6 | 2.6 | 0.3 | 2.4 |
| | | 29 | 95.0 | 2.8 | 0.3 | 1.9 |
| | | 48 | 95.2 | 3.8 | 0.4 | 0.7 |
| 1 kg/mt ds | 0.1 kg/mt ds | 21 | 94.6 | 2.5 | 0.3 | 2.4 |
| | | 24 | 95.1 | 2.6 | 0.3 | 2.0 |
| | | 29 | 95.4 | 2.9 | 0.3 | 1.4 |
| | | 48 | 95.3 | 3.7 | 0.4 | 0.7 |
| 1 kg/mt ds | 0.2 kg/mt ds | 21 | 95.1 | 2.5 | 0.3 | 2.0 |
| | | 24 | 95.3 | 2.6 | 0.3 | 1.7 |
| | | 29 | 95.5 | 2.9 | 0.4 | 1.2 |
| | | 48 | 95.4 | 3.7 | 0.4 | 0.5 |
| 1 kg/mt ds | 0.3 kg/mt ds | 21 | 95.6 | 2.5 | 0.3 | 1.7 |
| | | 24 | 95.7 | 2.6 | 0.3 | 1.4 |
| | | 29 | 95.7 | 2.9 | 0.3 | 1.1 |
| | | 48 | 95.3 | 3.6 | 0.3 | 0.7 |
| 1 kg/mt ds | 0.5 kg/mt ds | 21 | 95.6 | 2.6 | 0.3 | 1.4 |
| | | 24 | 95.9 | 2.6 | 0.3 | 1.2 |
| | | 29 | 95.9 | 2.9 | 0.3 | 0.9 |
| | | 48 | 95.2 | 3.8 | 0.4 | 0.7 |
| 0.5 kg/mt ds | 0.5 kg/mt ds | 21 | 94.2 | 2.0 | 0.4 | 3.4 |
| | | 24 | 94.5 | 2.5 | 0.4 | 3.0 |
| | | 29 | 95.3 | 2.1 | 0.4 | 2.3 |
| | | 48 | 95.9 | 2.5 | 0.3 | 1.3 |

The addition of TrAA to the saccharification reaction caused an increase in DP1, i.e., glucose, in the reaction. Optimal conditions for DP1 production were found where glucoamylase was at 1 kg/mt ds and TrAA was at 0.5 kg/mt ds. DP1 under these conditions reached 95.9% w/w ds, which was higher than the maximum level of DP1 obtained without TrAA, 95.2% w/w ds. The maximum level DP1 was reached after 24 hours in the presence of TrAA, but was reached only after 24 hours with glucoamylase alone. In the presence of 0.5 kg/mt ds and TrAA, reversion of DP1 to higher oligosaccharides did not begin until 48 hours after the reaction was initiated.

Example 4

TrAA is also useful for increasing the yield of maltose in a saccharification reaction. TrAA displays maltogenic activity at relatively low pH, as determined in the following experiment. The substrate consisted of a liquefied starch substrate prepared as described in Example 2, except that raw corn was diluted with water to create a slurry of 30% w/w ds, to which 0.25 kg/mt ds of Spezyme® Ethyl (Genencor International, Inc., Lot No. 107-04107-001) was added. After liquefaction at 92° C. for 25 min., the liquefied starch was cooled to 55° C. and pH was adjusted using 20% v/v sulfuric acid. DPn was measured as described in Example 2 above. FIG. 2 depicts the pH dependence of DP2 production after a 48 hour reaction catalyzed by 0.5 kg/mt ds TrAA (Lot No. GCI12004017/018-UF). As shown in FIG. 2, TrAA showed optimal activity at pH 5.0 to 5.5; however, TrAA also showed nearly optimum activity over a range of pH from 4.5 to 6.0. This experiment indicates that TrAA is highly active at the relatively low pH of 4.5.

Example 5

TrAA can catalyze the production of DP2 to levels comparable to those obtained with the maltogenic fungal α-amylase Clarase® L (Genencor International, Inc.). TrAA was produced from *T. reesei* and purified according to the procedures described in Example 1 above. The TrAA (Lot No. 150906) used for this experiment demonstrated a specific activity of about 18,000 SKBU/g. TrAA was also tested in combination with a pullulanase in the form of Optimax® L-1000 (Genencor International, Inc., Lot No. 107-04224-001), which had a specific activity of about 1040 PU units/g. The specific activity of the Clarase® L (Lot No. 107-04330-001) in this experiment was about 41,000 SKBU/g.

Figure 3:
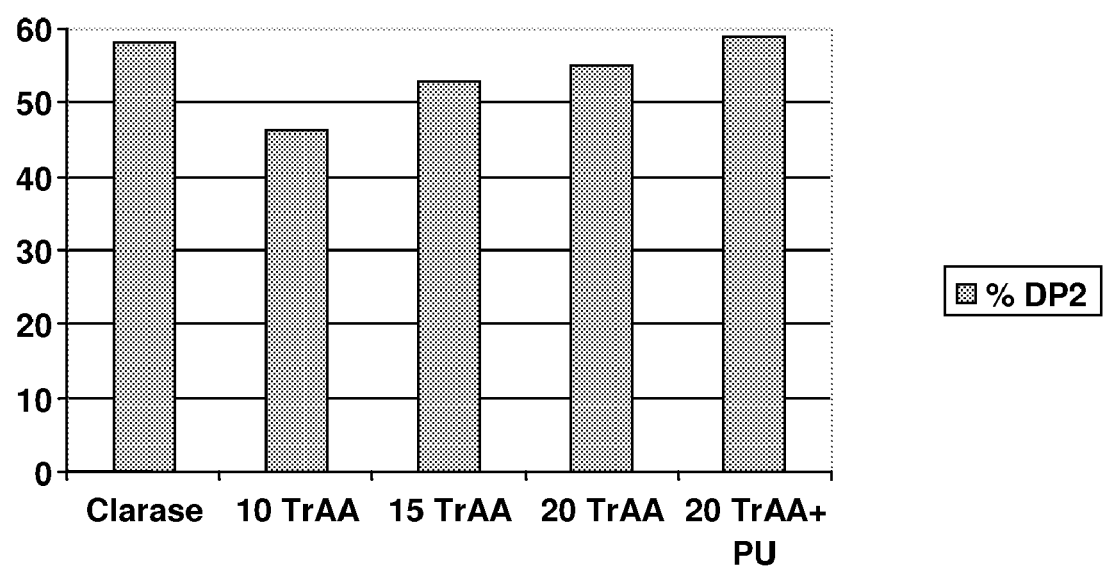
FIG. 3 depicts the ability of TrAA to catalyze the production of maltose with an efficiency comparable to Clarase® L. Weight percent of maltose (DP2) produced after 48 hours of a maltose production process is shown on the y-axis. The enzyme used to catalyze the reaction is shown on the x-axis. "Clarase": 10 SKBU/g ds of Clarase® L at pH 5.5, 55° C. "10 TrAA": 10 SKBU/g ds *Trichoderma reesei* α-amylase at pH 4.5, 60° C. "15 TrAA" and "20 TrAA" represent TrAA at 15 SKBU/g ds and 20 SKBU/g ds, respectively, at pH 4.5, 60° C. "20 TrAA+PU" represents the addition of 0.25 kg/mt ds pullulanase to 20 SKBU/g ds TrAA at pH 4.5, 60° C.

Liquefied starch was prepared as described in Example 2 and was adjusted to 55° C., pH 5.5, or 60° C., pH 4.5. Enzymes were added at the concentrations indicated below, and the reaction was run for 48 hours at the temperature indicated. DPn produced during the reaction were measured at 24 hours and 48 hours after the reaction was initiated, using the procedures described in Example 2. TABLE 3 shows the DPn obtained from a representative reaction. FIG. 3 depicts the concentration of DP2 obtained after 48 hours of the saccharification reaction as a function of enzyme concentration in units of SKBU/g.

TABLE 3

| Enzyme 1 (dose) | Enzyme 2 (dose) | T (° C.) | pH | Time (hr) | % DP1 | % DP2 | % DP3 | % HS |
|---|---|---|---|---|---|---|---|---|
| Clarase ® L (10 SKBU/g) | NA | 55 | 5.5 | 24 | 3.0 | 53.9 | 21.3 | 21.7 |
| | | | | 48 | 4.4 | 58.2 | 17.1 | 20.3 |
| TrAA (10 SKBU/g) | NA | 60 | 4.5 | 24 | 4.5 | 37.8 | 23.7 | 34.0 |
| | | | | 48 | 6.4 | 46.2 | 21.7 | 25.7 |
| TrAA (15 SKBU/g) | NA | 60 | 4.5 | 24 | 6.7 | 47.4 | 21.3 | 24.6 |
| | | | | 48 | 8.9 | 52.8 | 17.3 | 21.1 |
| TrAA (20 SKBU/g) | NA | 60 | 4.5 | 24 | 8.7 | 52.6 | 17.6 | 21.1 |
| | | | | 48 | 10.5 | 55.1 | 14.5 | 19.9 |
| TrAA (20 SKBU/g) | PU (0.25 kg/mt) | 60 | 4.5 | 24 | 8.9 | 54.5 | 19.4 | 17.2 |
| | | | | 48 | 11.3 | 58.9 | 16.5 | 13.4 |

By 48 hours, DP2 concentration had risen to about 58% w/w ds in the presence of 10 SKBU/g Clarase® L at 55° C., pH 5.5. By comparison, reactions catalyzed by 20 SKBU/g TrAA at 60° C., pH 4.5 produced about 55% DP2 by 48 hours. In the presence of 20 SKBU/g TrAA and 0.25 kg/mt pullulanase, however, DP2 rose to about 59% w/w ds in 48 hours, exceeding the concentration obtained with Clarase® L. Further, TrAA by itself or in combination with a pullulanase produced a maltose-rich syrup with a higher concentration of DP1 than obtained with Clarase® L: about 11% w/w ds versus about 4% w/w ds. This experiment accordingly shows that TrAA can be used to produce a high maltose syrup at a low pH, where the syrup contains comparable levels of maltose, as well as higher levels of glucose, than those obtained with Clarase® L.

Example 6

When used at low pH, TrAA significantly outperformed other conventional maltogenic amylases, as show in the following experiment. The experimental conditions used were the same as in Example 5, except that the reaction was conducted at 58° C., pH 4.6 and DPn production was catalyzed by 0.2 kg/mt ds BBA (a β-amylase; Lot No. 05189-001), 0.2 kg/mt ds Clarase® L (Lot No. 9016231002), or 0.5 kg/mt ds TrAA (Lot No. GCI2004017/018-UF). As indicated in TABLE 4, significantly higher DP2 concentrations were obtained in the presence of TrAA then either BBA or Clarase® L.

TABLE 4

| Enzyme (dose) | T (° C.) | pH | Time (hr) | % DP1 | % DP2 | % DP3 | % HS | DE |
|---|---|---|---|---|---|---|---|---|
| BBA (0.2 kg/mt ds) | 58 | 4.6 | 24 | 0.6 | 12.5 | 3.2 | 83.6 | 25 |
| | | | 48 | 0.3 | 12.2 | 3.1 | 84.4 | 24 |
| Clarase ® L (0.2 kg/mt ds) | 58 | 4.6 | 24 | 0.6 | 9.9 | 17.9 | 71.6 | 28 |
| | | | 48 | 10.0 | 18.0 | 14.2 | 71.3 | 28 |
| TrAA (0.5 kg/mt ds) | 58 | 4.6 | 24 | 6.0 | 44.4 | 20.8 | 28.7 | 46 |
| | | | 48 | 8.1 | 51.2 | 17.8 | 22.9 | 49 |

Example 7

Figure 4:
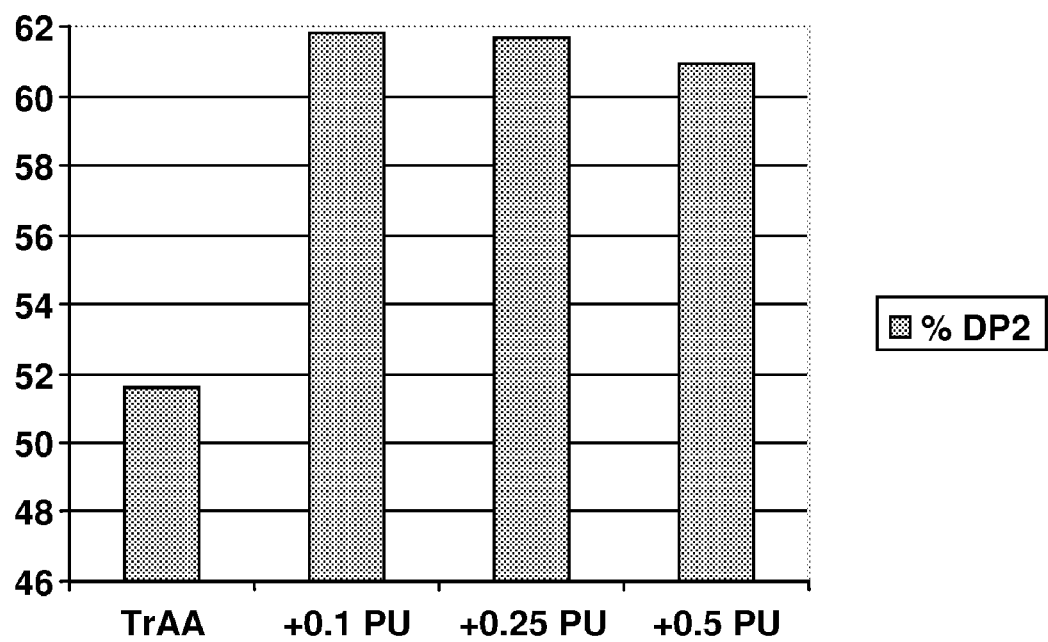
FIG. 4 depicts a maltose production process catalyzed by TrAA in the optimal amount of pullulanase. The y-axis shows the weight percent of maltose (DP2) produced after 48 hours at pH 4.6, 58° C. in the presence of 0.5 kg/mt ds TrAA. The x-axis shows the amount of pullulanase in kg/mt ds added to the reaction.

DP2 production by TrAA was significantly increased by the addition of a pullulanase. In the following experiment, the experimental conditions were the same as described in Example 5, except that the reaction was at 58° C., pH 4.6. Pullulanase was added in the form of Optimax® L-1000 (Genencor International, Inc.; Lot No. 9016167004 at 1165 PU/g) at the concentrations indicated in TABLE 5. The reaction was run at 58° C., pH 4.6, for the times indicated. As shown in TABLE 5, 0.1-0.25 kg/mt ds pullulanase significantly increased DP2 production catalyzed by TrAA by 48 hours. FIG. 4 depicts DP2 formation at 48 hours under the various conditions described in this example.

TABLE 5

| TrAA | PU | T (° C.) | pH | Time (hr) | % DP1 | % DP2 | % DP3 | % HS | DE |
|---|---|---|---|---|---|---|---|---|---|
| 0.5 kg/mt ds | None | 58 | 4.6 | 24 | 7.2 | 44.8 | 20.1 | 27.9 | 47 |
| | | | | 48 | 9.2 | 51.6 | 16.8 | 22.3 | 50 |
| 0.5 kg/mt ds | 0.1 kg/mt ds | 58 | 4.6 | 24 | 6.7 | 44.9 | 21.5 | 26.9 | 47 |
| | | | | 48 | 10.4 | 61.8 | 22.4 | 5.3 | 57 |

TABLE 5-continued

| TrAA | PU | T (°C.) | pH | Time (hr) | % DP1 | % DP2 | % DP3 | % HS | DE |
|---|---|---|---|---|---|---|---|---|---|
| 0.5 kg/mt ds | 0.25 kg/mt ds | 58 | 4.6 | 24 | 7.8 | 49.4 | 23.6 | 19.2 | 50 |
| | | | | 48 | 10.8 | 61.7 | 22.0 | 5.5 | 57 |
| 0.5 kg/mt ds | 0.5 kg/mt ds | 58 | 4.6 | 24 | 7.5 | 50.3 | 25.0 | 17.2 | 51 |
| | | | | 48 | 10.3 | 60.9 | 22.9 | 5.9 | 56 |

All references cited above are herein incorporated by reference in their entirety for all purposes.

What is claimed is:

1. An isolated polypeptide comprising (i) residues 21-463 of SEQ ID NO:3, or (ii) a variant of *Trichoderma reesei* α-amylase (TrAA), wherein the variant has α-amylase activity and at least 90% amino acid sequence identity to residues 21-463 of SEQ ID NO:3.

2. The isolated polypeptide of claim 1, wherein said variant has at least 95% sequence identity to residues 21-463 of SEQ ID NO:3.

3. The isolated polypeptide of claim 2, wherein the variant has at least 99% sequence identity to residues 21-463 of SEQ ID NO:3.

4. The isolated polypeptide of claim 1, wherein the variant has 1-10 amino acid substitutions, insertions, or deletions compared to residues 21-463 of SEQ ID NO:3.

5. The isolated polypeptide of claim 1 comprising SEQ ID NO:3.

6. The isolated polypeptide of claim 1 consisting of residues 21-463 of SEQ ID NO:3.

7. A starch processing composition comprising the polypeptide of claim 1.

* * * * *

SEQUENCE LISTING

<160> NUMBER OF SEQ ID NOS: 7

<210> SEQ ID NO 1
<211> LENGTH: 1548
<212> TYPE: DNA
<213> ORGANISM: Trichoderma reesei

<400> SEQUENCE: 1

```
atgaagctcc ggtacgctct cccgctgctc ttgcagctct ctttgccggt cctctccgca      60
gacaccgccg cctggaggtc cgcaccatc tactttgccc tgacagaccg catcgctcgt     120
ggaagcggtg acacgggggg cagtgcgtgt gggaacctgg gggactactg cggtggcacg     180
ttccagggct tggagagcaa gttggactac atcaagggca tgggattcga tgccatctgg     240
atcacacctg ttgtgacgag tgagtctttt cataccttgc cctgccttgc ctcgcctcgc     300
cttgcatgtg tcgcatacag gcttctggta tgcatagcta aacctgatac ctctggacag     360
acagtgatgg gggctaccat ggctattggg cggaggacat cgactccatc aactctcatt     420
atggctctgc ggacgatctc aagagtctcg tcaacgccgc gcatagcaag gtattccctt     480
ttgttcacac cagacttcat gattatcaaa attaacacaa accagggctt ctatatgatg     540
gtggacgtcg tggccaacca catgggctac gccaatatct ctgacgatag tccctctcca     600
ctgaaccagg cctcgtcgta tcaccccgag tgtgatatcg actacaacaa ccaaaccagc     660
gtcgagaact gctggatcag cggcctcccg gatctcaaca gcagagctc aaccatccgc     720
agcctctacc aggactgggt ctccaacctc gtgtccacgt acggcttcga cggcgtccgc     780
atcgacaccg tcaagcacgt cgagcaagac tactggcccg gcttcgtcaa cgccaccggc     840
gtctactgca tcggcgaggt cttcgacgga gacccaaact acctgctgcc ctacgccagc     900
ctcatgccgg gcctgctcaa ctacgccatc tactacccca tgacgcgctt cttcctccag     960
cagggctcct cgcaggacat ggtcaacatg cacgaccaga tcggcagcat gttccccgac    1020
ccgaccgcgc tcggcacctt tgtcgacaac cacgacaacc gcgcttcct gagcatcaag    1080
aacgacacgg ccctgctcaa gaacgcgctg acgtacacca tcctctcgcg cggcatcccc    1140
atcgtctact acggcaccga gcaggccttc tcgggcggca acgacccggc caacagggag    1200
gacctctggc gcagcggctt caacgcccag tccgacatgt acgacgccat ctccaagctc    1260
acctacgcca agcacgccgt cggcggcctc gccgacaacg accacaagca cctgtacgtc    1320
gccgacacgg cctacgcctt cagccgcgcc ggcggcaaca tggtggccct gaccaccaac    1380
agcggcagcg ggagctcggc ccagcactgc ttcggcacgc aggtgcccaa cggccgctgg    1440
cagaatgtct ttgacgaggg caatgggccg acgtattccg ccgacggcaa cggccagctt    1500
tgcttgaatg tgtccaacgg tcagcccatt gtcttgctgt cttcgtga                1548
```

<210> SEQ ID NO 2
<211> LENGTH: 1392
<212> TYPE: DNA
<213> ORGANISM: Trichoderma reesei

<400> SEQUENCE: 2

```
atgaagctcc ggtacgctct cccgctgctc ttgcagctct ctttgccggt cctctccgca     60
gacaccgccg cctggaggtc ccgcaccatc tactttgccc tgacagaccg catcgctcgt    120
ggaagcggtg acacgggggg cagtgcgtgt gggaacctgg ggactactg cggtggcacg     180
ttccagggct tggagagcaa gttgactac atcaagggca tgggattcga tgccatctgg    240
atcacacctg ttgtgacgag tgatgatggg ggctaccatg gctattgggc ggaggacatc    300
gactccatca actctcatta tggctctgcg gacgatctca gagtctcgt caacgccgcg    360
catagcaagg gcttctatat gatggtggac gtcgtggcca accacatggg ctacgccaat    420
atctctgacg atagtccctc tccactgaac caggcctcgt cgtatcaccc cgagtgtgat    480
atcgactaca caaccaaac cagcgtcgag aactgctgga tcagcggcct cccggatctc    540
aacacgcaga gctcaaccat ccgcagcctc taccaggact gggtctccaa cctcgtgtcc    600
acgtacggct tcgacggcgt ccgcatcgac accgtcaagc acgtcgagca agactactgg    660
cccggcttcg tcaacgccac cggcgtctac tgcatcggcg aggtcttga cggagaccca    720
aactacctgc tgccctacgc cagcctcatg ccgggcctgc tcaactacgc catctactac    780
cccatgacgc gcttcttcct ccagcagggc tcctcgcagg acatggtcaa catgcacgac    840
cagatcggca gcatgttccc cgacccgacc gcgctcggca cctttgtcga caaccacgac    900
aacccgcgct tcctgagcat caagaacgac acggccctgc tcaagaacgc gctgacgtac    960
accatcctct cgcgcggcat ccccatcgtc tactacggca ccgagcaggc cttctcgggc   1020
ggcaacgacc cggccaacag ggaggacctc tggcgcagcg gcttcaacgc ccagtccgac   1080
atgtacgacg ccatctccaa gctcacctac gccaagcacg ccgtcggcgg cctcgccgac   1140
aacgaccaca gcacctgta cgtcgccgac acggcctacg ccttcagccg cgccggcggc   1200
aacatggtgg ccctgaccac caacagcggc agcgggagct cggcccagca ctgcttcggc   1260
acgcaggtgc ccaacggccg ctggcagaat gtctttgacg agggcaatgg ccgacgtat   1320
tccgccgacg gcaacgggcca gctttgcttg aatgtgtcca cggtcagcc cattgtcttg   1380
ctgtcttcgt ga                                                       1392
```

<210> SEQ ID NO 3
<211> LENGTH: 463
<212> TYPE: PRT
<213> ORGANISM: Trichoderma reesei

<400> SEQUENCE: 3

```
Met Lys Leu Arg Tyr Ala Leu Pro Leu Leu Gln Leu Ser Leu Pro
1               5                   10                  15

Val Leu Ser Ala Asp Thr Ala Ala Trp Arg Ser Arg Thr Ile Tyr Phe
            20                  25                  30

Ala Leu Thr Asp Arg Ile Ala Arg Gly Ser Gly Asp Thr Gly Gly Ser
        35                  40                  45

Ala Cys Gly Asn Leu Gly Asp Tyr Cys Gly Gly Thr Phe Gln Gly Leu
    50                  55                  60

Glu Ser Lys Leu Asp Tyr Ile Lys Gly Met Gly Phe Asp Ala Ile Trp
65                  70                  75                  80

Ile Thr Pro Val Val Thr Ser Asp Asp Gly Gly Tyr His Gly Tyr Trp
```

```
                85                  90                  95
Ala Glu Asp Ile Asp Ser Ile Asn Ser His Tyr Gly Ser Ala Asp Asp
            100                 105                 110

Leu Lys Ser Leu Val Asn Ala Ala His Ser Lys Gly Phe Tyr Met Met
        115                 120                 125

Val Asp Val Ala Asn His Met Gly Tyr Ala Asn Ile Ser Asp Asp
    130                 135                 140

Ser Pro Ser Pro Leu Asn Gln Ala Ser Ser Tyr His Pro Glu Cys Asp
145                 150                 155                 160

Ile Asp Tyr Asn Asn Gln Thr Ser Val Glu Asn Cys Trp Ile Ser Gly
                165                 170                 175

Leu Pro Asp Leu Asn Thr Gln Ser Ser Thr Ile Arg Ser Leu Tyr Gln
            180                 185                 190

Asp Trp Val Ser Asn Leu Val Ser Thr Tyr Gly Phe Asp Gly Val Arg
        195                 200                 205

Ile Asp Thr Val Lys His Val Glu Gln Asp Tyr Trp Pro Gly Phe Val
    210                 215                 220

Asn Ala Thr Gly Val Tyr Cys Ile Gly Glu Val Phe Asp Gly Asp Pro
225                 230                 235                 240

Asn Tyr Leu Leu Pro Tyr Ala Ser Leu Met Pro Gly Leu Leu Asn Tyr
                245                 250                 255

Ala Ile Tyr Tyr Pro Met Thr Arg Phe Phe Leu Gln Gln Gly Ser Ser
            260                 265                 270

Gln Asp Met Val Asn Met His Asp Gln Ile Gly Ser Met Phe Pro Asp
        275                 280                 285

Pro Thr Ala Leu Gly Thr Phe Val Asp Asn His Asp Asn Pro Arg Phe
    290                 295                 300

Leu Ser Ile Lys Asn Asp Thr Ala Leu Leu Lys Asn Ala Leu Thr Tyr
305                 310                 315                 320

Thr Ile Leu Ser Arg Gly Ile Pro Ile Val Tyr Tyr Gly Thr Glu Gln
                325                 330                 335

Ala Phe Ser Gly Gly Asn Asp Pro Ala Asn Arg Glu Asp Leu Trp Arg
            340                 345                 350

Ser Gly Phe Asn Ala Gln Ser Asp Met Tyr Asp Ala Ile Ser Lys Leu
        355                 360                 365

Thr Tyr Ala Lys His Ala Val Gly Gly Leu Ala Asp Asn Asp His Lys
    370                 375                 380

His Leu Tyr Val Ala Asp Thr Ala Tyr Ala Phe Ser Arg Ala Gly Gly
385                 390                 395                 400

Asn Met Val Ala Leu Thr Thr Asn Ser Gly Ser Gly Ser Ser Ala Gln
                405                 410                 415

His Cys Phe Gly Thr Gln Val Pro Asn Gly Arg Trp Gln Asn Val Phe
            420                 425                 430

Asp Glu Gly Asn Gly Pro Thr Tyr Ser Ala Asp Gly Asn Gly Gln Leu
        435                 440                 445

Cys Leu Asn Val Ser Asn Gly Gln Pro Ile Val Leu Leu Ser Ser
    450                 455                 460

<210> SEQ ID NO 4
<211> LENGTH: 60
<212> TYPE: DNA
<213> ORGANISM: Trichoderma reesei

<400> SEQUENCE: 4
atgaagctcc ggtacgctct cccgctgctc ttgcagctct ctttgccggt cctctccgca      60
```

```
<210> SEQ ID NO 5
<211> LENGTH: 20
<212> TYPE: PRT
<213> ORGANISM: Trichoderma reesei

<400> SEQUENCE: 5

Met Lys Leu Arg Tyr Ala Leu Pro Leu Leu Leu Gln Leu Ser Leu Pro
1               5                   10                  15

Val Leu Ser Ala
            20

<210> SEQ ID NO 6
<211> LENGTH: 22
<212> TYPE: DNA
<213> ORGANISM: Artificial
<220> FEATURE:
<223> OTHER INFORMATION: synthetic primer

<400> SEQUENCE: 6
atgaagctcc ggtacgctct cc                                              22

<210> SEQ ID NO 7
<211> LENGTH: 25
<212> TYPE: DNA
<213> ORGANISM: Artificial
<220> FEATURE:
<223> OTHER INFORMATION: synthetic primer

<400> SEQUENCE: 7
tcacgaagac agcaagacaa tgggc                                           25
```